(12) United States Patent
Irvin et al.

(10) Patent No.: US 8,961,984 B2
(45) Date of Patent: *Feb. 24, 2015

(54) SURFACE-COATED STRUCTURES AND METHODS

(75) Inventors: Randall T. Irvin, Sherwood Park (CA); Elisabeth M. Davis, Edmonton (CA); DongYang Li, Edmonton (CA)

(73) Assignee: Arch Biophysics, Inc., Alberta (CA)

( * ) Notice: Subject to any disclaimer, the term of this patent is extended or adjusted under 35 U.S.C. 154(b) by 1077 days.

This patent is subject to a terminal disclaimer.

(21) Appl. No.: 12/899,958

(22) Filed: Oct. 7, 2010

(65) Prior Publication Data

US 2011/0087321 A1     Apr. 14, 2011

Related U.S. Application Data

(60) Provisional application No. 61/249,934, filed on Oct. 8, 2009.

(51) Int. Cl.
| | |
|---|---|
| *A61K 39/00* | (2006.01) |
| *A61K 39/108* | (2006.01) |
| *A61K 39/02* | (2006.01) |
| *C07K 14/21* | (2006.01) |
| *A61B 5/145* | (2006.01) |
| *A61L 27/04* | (2006.01) |
| *A61L 27/34* | (2006.01) |
| *A61L 27/54* | (2006.01) |
| *A61L 31/02* | (2006.01) |
| *A61L 31/04* | (2006.01) |
| *A61L 31/10* | (2006.01) |
| *A61L 31/16* | (2006.01) |
| *C12N 15/10* | (2006.01) |

(52) U.S. Cl.
CPC ............. *C07K 14/21* (2013.01); *A61B 5/14532* (2013.01); *A61B 5/14546* (2013.01); *A61L 27/04* (2013.01); *A61L 27/34* (2013.01); *A61L 27/54* (2013.01); *A61L 31/022* (2013.01); *A61L 31/047* (2013.01); *A61L 31/10* (2013.01); *A61L 31/16* (2013.01); *C12N 15/1037* (2013.01); *A61L 2400/18* (2013.01)
USPC .................. 424/185.1; 424/184.1; 424/234.1; 424/260.1

(58) Field of Classification Search
CPC ....... A61K 38/16; A61K 39/02; A61K 39/104
USPC ...................... 424/184.1, 185.1, 234.1, 260.1
See application file for complete search history.

(56) References Cited

FOREIGN PATENT DOCUMENTS

WO    WO 2007/089272 A    8/2007

OTHER PUBLICATIONS

Giltner et al., "The *Pseudomonas aeruginosa* type IV pllin receptor binding domain functions as an adhesion for both biotic and abiotic surfaces", Molecular Microbiology, vol. 59, No. 4, pp. 1083-1096 (2006)
International Search Report from relation PCT Patent Application No. PCT/CA2010/001612 mailed on Jan. 19, 2011, Application now published as International Publication No. WO 2011/041906 on Apr. 14, 2011.
Lombardo et al., "Initial studies of protein nanotube oligomerization from a modified gold surface", J. Bionanoscience, vol. 3, No. 1, pp. 61-65 (2009).
Yu et al., "Surface nanocrystallization of stainless steel for reduced biofilm adherence", Nanotechnolgy, vol. 19, pp. 1-8 (2008).

*Primary Examiner* — Rodney P Swartz
(74) *Attorney, Agent, or Firm* — King & Spalding

(57) ABSTRACT

The present invention relates to a method for covalently attaching a compound to a stainless steel, tin, iron, or titanium substrate, by contacting exposed surface(s) of the substrate with a synthetic pilin peptide containing a disulfide loop derived from the C-terminal receptor binding protein of Type IV *P. aeruginosa* (T4P) pilin, to bind the pilin peptide to the exposed surface(s), and covalently attaching the compound to the pilin peptide. Also disclosed are a substrate formed by the method and a biosensor device that uses the uses. Also disclosed are methods for improving the corrosion resistance, adhesive force, hardness and electron work function of certain metals.

21 Claims, 20 Drawing Sheets

```
G7-G9      SIDWGCASDSNAVSSGTDRNMPALTAGTLPARFAPSECR  SEQ ID NO:1
PA110594   TIDWACTSASNAT--ATAQGFTGMAAGSVPQEFAPAQCR    SEQ ID NO:2
PAO        DGVWACKSTQDPMFTPKGCDN                      SEQ ID NO:3
PAK        DGLWKCTSDQDEQFIPKGCSR                      SEQ ID NO:4
PA1244     DGVWNCKITKTPTAWKPNYAPANCPKS                SEQ ID NO:5
PA5659     EGVWTCATSGSPANWKANYAPANCPKS                SEQ ID NO:6
PA92935    NGGWSCATTVDAKFRPNGCTD                      SEQ ID NO:7
PA5196     GSSWACGNASIDGFAGTGTTIDAKYLPNACKP           SEQ ID NO:8
K122-4     SYTWACTSNADNKYLPKTCQTATTTTP                SEQ ID NO:9
Composite: K/A/S/T-C-T/K/A-S/T-D/T/N-Q/V/A-D/E-E/P/A/N-Q/M/K-F/Y-I/T/R/L-P-K/N-G/T-C-S/D/T/Q/N-
K/N/D/T (SEQ ID NO:10).
Composite S/T-I-D-W-G/A-C-A/T-S-D/A-S-N-A-V/T-S/--S--G/A-T-D/A-R/Q-N/G-M/F-P/T-A/G-L/M-T/A-A-G-
T/S-L/V-P-A/Q-R/E-F-A-P-S/A-E/Q-C-R (SEQ ID NO:21)
```

Fig. 1A

```
K122-4        SYTWACT S----NADNKYLPKTCQTA-----TTTTP     SEQ ID NO:11
Rmet2278954   SVTWQCE S----SADKRYVPQACAKASESGKTTTTTT    SEQ ID NO:12
Ncin7259486   SFSWVCK KGTSDSVDDKFLPSSCRTA-----ATTTAG    SEQ ID NO:13
Ecor729393    SFSWECS S----NADAKYLPSSCRNA-----ATPTPT    SEQ ID NO:14
```

Fig. 1B

```
PA5196        GSSWACGNASIDG--------FAGTGTTIDAKYLPNACKP-------  SEQ ID NO:15
Ecor729393    SFSWECSS------------------NADAKYLPSSCRNAATPTPTP  SEQ ID NO:16
Ngon95402     SVKWFCGQPVTRTGDNDTVADAKDGKEIDTKHLPSTCRDTSSAGK-   SEQ ID NO:17
Xcam21232529  SISWGCTN----------------GTTIDQKYLPTSCRTAAAP----  SEQ ID NO:18
```

Fig. 1C

```
PA92935       NGGWSCATTVDAKFRPNGCTD----   SEQ ID NO: 19
Dnod120452    SGSWYCHSNAAEKFLPSGCKYDASL    SEQ ID NO: 20
PA92935       NGGWSCATTVDAKFRPNGCTD----   SEQ ID NO: 19
Dnod120452    SGSWYCHSNAAEKFLPSGCKYDASL    SEQ ID NO: 20
```

Fig. 1D

Rmet = Ralsonia metallidurans GI 2278954
Ncin= Neisseria cinera GI 7259486
Ecor= Eikenella corrodens GI 729393
Ngon= Neisseria gonorrhoeae GI 95402
Xcam= Xanthomonas campestris GI 21232529
Dnod= Dichelobacter nodosus GI 120452

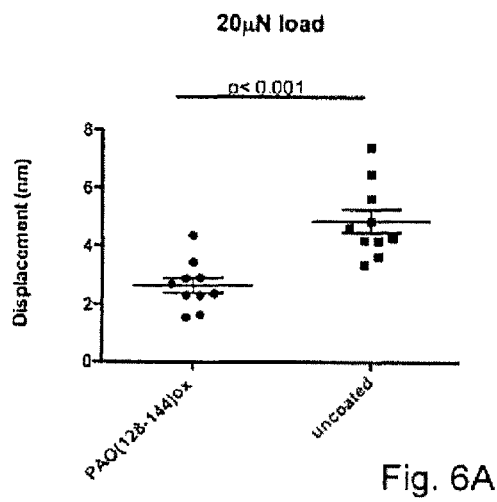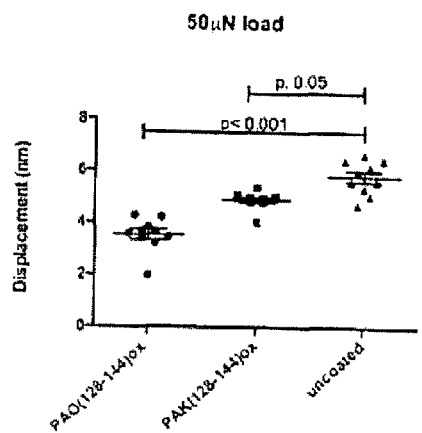
Fig. 6A  Fig. 6B
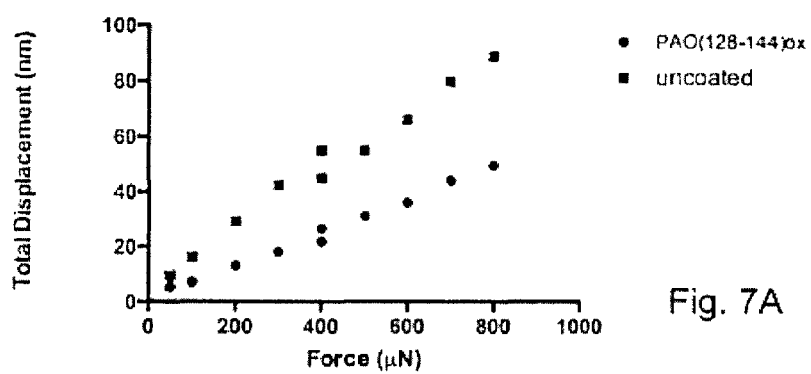
Fig. 7A
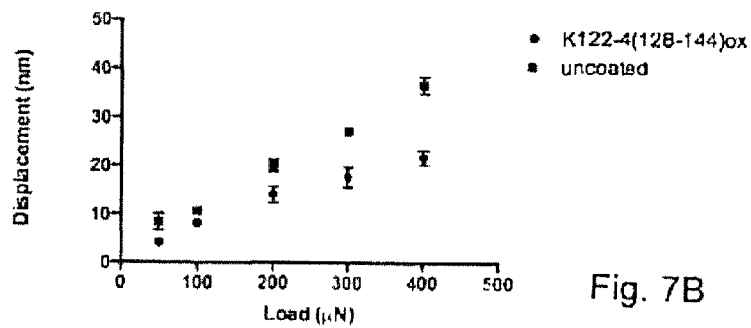
Fig. 7B

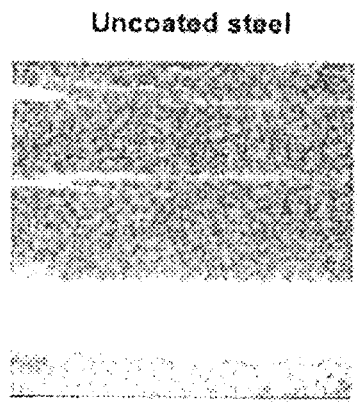
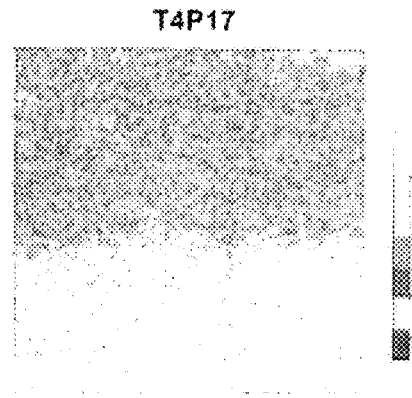
Fig. 8A                    Fig. 8B
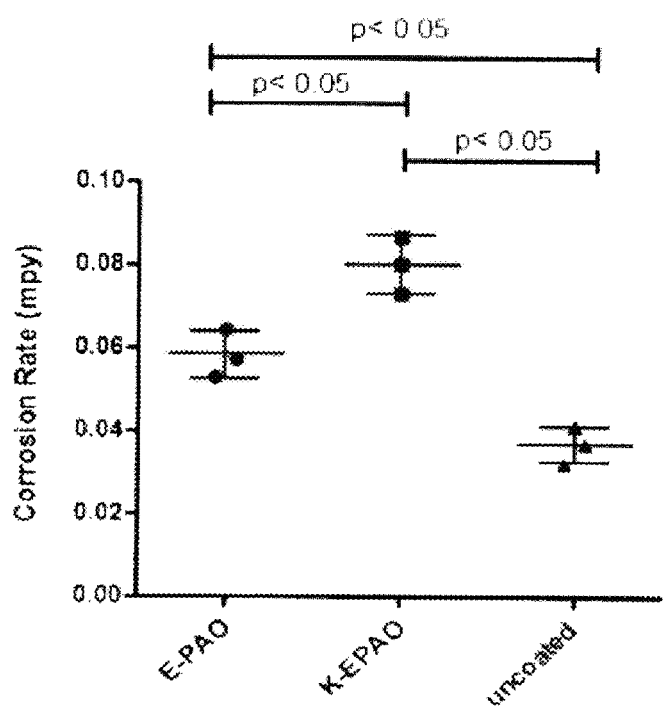
Fig. 11

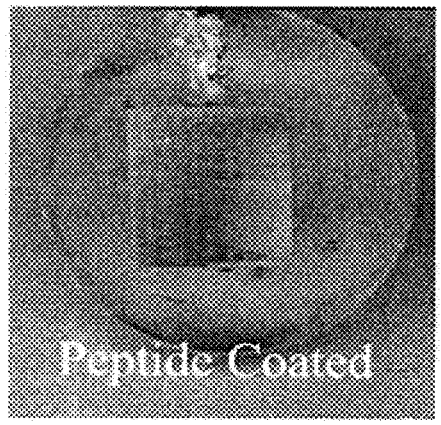
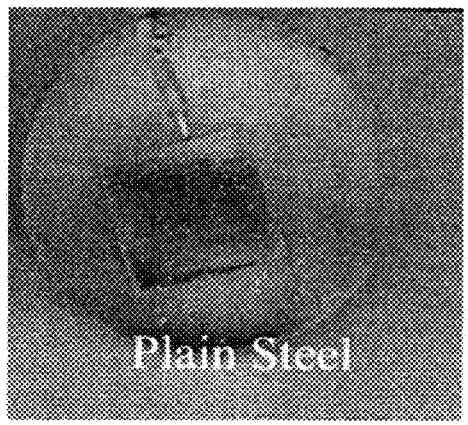
Fig. 12A        Fig. 12B
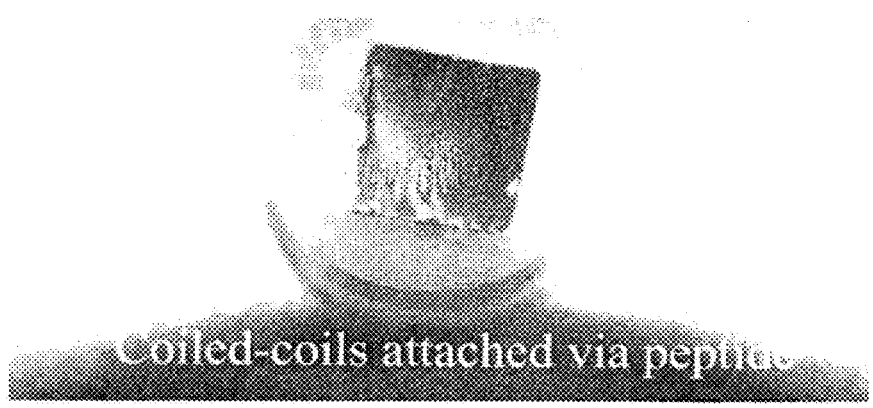
Fig. 12C

SURFACE-COATED STRUCTURES AND METHODS

This patent application claims the benefit of priority to U.S. Provisional Patent Application No. 61/249,934 filed on Oct. 8, 2009, which is incorporated in its entirety herein by reference.

FIELD OF THE INVENTION

The present invention relates to the field of material coatings that employ a Type IV *P. aeruginosa* (T4P) pilin peptide, and to applications thereof.

BACKGROUND

Bacterial Type IV pili are essential for host colonization and virulence for many Gram negative bacteria, and may also play a role in pathogenesis for some Gram positive bacteria. Type IV pili extend from the bacterial surface and mediate specific adherence to biotic and abiotic surfaces. The pili binding domain responsible for this binding is encoded within a 12-17 disulfide loop region located in the C-terminal region of the protein, and synthetic peptides containing this region only, e.g., a disulfide-loop peptide composed of residues 128-144 from the *Pseudomonas aeruginosa* Type IV pilin, have been shown to bind to biotic and abiotic surfaces.

The present inventors and colleagues have recently shown that pilin-derived protein nanotubes (PNTs) bind to stainless steel with high affinity, and the binding event was shown to be C-terminal tip-associated through competitive inhibition of PNT binding by synthetic peptides corresponding to the Type IV pilin peptide binding domains. (Yu, B. et al., J. Bionanoscience, 1:73-83 (2007). It was then further demonstrated by the present inventors and colleagues that pilin peptides derived from the C-terminal receptor binding domain, when bound to abiotic surfaces such as stainless steel, tin, aluminum, titanium, chromium, plastic, glass, silicate, ceramics, and mixtures thereof, were able to inhibit bacterial biofilm formation on the coated surfaces (U.S. 20080287367).

It has now been discovered that binding of synthetic pilin peptide containing a disulfide loop derived from the C-terminal receptor binding protein of Type IV *P. aeruginosa* (T4P) pilin to some metals significantly enhances certain surface properties of the metal, i.e., independent of biofilm formation, and in some metals alters the electronic properties of the surfaces in ways that can be exploited, for example, in biosensor applications.

SUMMARY OF THE INVENTION

In one aspect, the invention includes a method of covalently attaching a compound to one or more exposed surfaces of a substrate formed of stainless steel, tin, iron, or titanium. The method includes (i) contacting exposed surface(s) of the material with a synthetic peptide containing a disulfide loop derived from the C-terminal receptor binding protein of Type IV *P. aeruginosa* (T4P) pilin and containing 0-10, preferably 0-5 additional residues on either or both the N- or C-terminal side of the loop, to bind the pilin peptide covalently to the exposed surface(s), and (ii) before or after binding the peptide to the substrate, covalently attaching the compound to the pilin peptide, either directly or indirectly. The contacting step may preferentially localize the compound at exposed grain boundary regions of the material.

The pilin peptide may be formed with L-amino acids, D-amino acids, a mixture of D- and L-amino acids, or with D-amino acids in a retro-inverso form.

A preferred T4P pilin peptide contains the sequence K/A/S/T-C-T/K/A-S/T-D/T/N-Q/V/A-D/E-E/P/A/N-Q/M/K-F/Y-I/T/R/L-P-K/N-G/T-C-S/D/T/Q/N-K/N/D/T (SEQ ID NO:10). Exemplary peptides contain the sequence identified as SEQ ID NOS: 3, 4, or 9.

Another preferred T4P pilin peptide contains the sequence S/T-I-D-W-G/A-C-AT-S-D/A-S-N-A-V/T-S/--S--G/A-T-D/A-R/Q-N/G-M/F-P/T-A/G-L/M-T/A-A-G-T/S-L/V-P-NQ-R/E-F-A-P-S/A-E/Q-C-R (SEQ ID NO:11). Exemplary peptides contain the sequence identified as SEQ ID NOS: 1 and 2.

Where the substrate is porous or reticulated, the coating step may be carried out to bind the pilin peptide to internal surfaces defined by pores or reticulations in the material.

Exemplary compounds for attachment to the substrate include polypeptides, oligosaccharides, lipids, nucleic acids, and small organic molecules.

Other substrate metals contemplated in the method are transition metals from rows 4-6 and columns 9-12 of the period table, including cobalt, nickel, copper, zinc, ruthenium, rhodium, palladium, silver, cadmium, osmium, platinum, gold, chromium, and mercury, and mixtures and alloys thereof, and the metalloids silicon and germanium, and oxides thereof.

Also disclosed is a stainless steel, tin, iron, or titanium substrate with a covalently attached compound formed by the above method. The substrate has a altered work function by virtue of the covalent attachment of the T4P pilin peptide to the surface of the substrate. The substrate may be part of an implantable medical device, where the covalently attached compound (attached directly or indirectly) is preferably a bioactive compound, for example, a bone morphogenic factor. Alternatively, the substrate may be employed as a current sensor element in a biosensor device for detecting a change in current flow across the substrate surface in response to binding of an analyte-related ligand to a surface-bound receptor, where the receptor is directly attached to the pilin peptide or indirectly attached to the pilin peptide through a high-affinity binding pair, such as a biotin/avidin pair or leucine-zipper coiled-coil pair.

In a more general aspect, which takes advantage of the high-affinity binding of the pilin peptide to a variety of materials, including glass, polymers, latex, silicates (see below), the invention includes a method of attaching a non-pilin derived compound to a device having a surface composed of one or these materials by attaching a pilin peptide to such surface, and before or after such attachment, covalently attaching the compound, either directly or indirectly, to the pilin peptide. As above, indirect attachment may be through a high-affinity binding pair. A coated device formed by this method is also contemplated.

More generally, the analyte-detection device may include an analyte-detection device having a metal, plastic, ceramic, glass, or silicate substrate having a compound attached to the substrate surface by means of a synthetic peptide containing a disulfide loop derived from the C-terminal receptor binding protein of Type IV *P. aeruginosa* (T4P) pilin the substrate, and to which the compound is covalently attached. The device includes a detector for detecting the binding of an analyte-related molecule to the compound on the substrate.

The invention also includes an improvement in a method of treating stainless steel, tin, iron, or titanium metal material having surfaces with exposed grain boundary regions, to increase the surface hardness and reduce the rate of corrosion or the material. The method includes contacting exposed surfaces boundary regions in the material with a synthetic pilin peptide containing a disulfide loop derived from the C-terminal receptor binding protein of Type IV *P. aeruginosa* (T4P) pilin and containing 0-10, preferably 0-5, additional residues on either or both the N- or C-terminal side of the loop, under conditions effective to alter the electron work function of exposed grain-boundary regions by at least 0.2 EFW units and to increase the hardness of exposed grain-boundary regions, as measured by nano-indentation produced striking the metal surface with the tip of an atomic force microscope with a given force, by at least 20%.

Other metals contemplated in the method are transition metals from rows 4-6 and columns 9-12 of the period table, including cobalt, nickel, copper, zinc, ruthenium, rhodium, palladium, silver, cadmium, osmium, platinum, gold, chromium, and mercury, and mixtures and alloys thereof, and the metalloids silicon and germanium, and oxides thereof.

Where the structure is stainless steel, the coating may be effective to reduce the rate of corrosion of the coated surface, as measured by the corrosion current across the surface by at least 30%. Where the material is porous or reticulated, the coating step may be carried out to bind the pilin peptide to internal surfaces defined by pores or reticulations in the material. The contacting step may be effective to bind the pilin peptide selectively to said grain boundary regions, thus enhancing the hardness and corrosion resistance of the metal surface by preferentially protecting the surface at its grain boundary regions.

The pilin peptide may be formed with L-amino acids, D-amino acids, a mixture of D- and L-amino acids, or with D-amino acids in a retro-inverso form.

A preferred T4P pilin peptide contains the sequence K/A/S/T-C-T/K/A-S/T-D/T/N-Q/V/A-D/E-E/P/A/N-Q/M/K-F/Y-I/T/R/L-P-K/N-G/T-C-S/D/T/Q/N-K/N/D/T (SEQ ID NO:10). Exemplary peptides contain the sequence identified as SEQ ID NOS: 3, 4, or 9.

Another preferred T4P pilin peptide contains the sequence S/T-I-D-W-G/A-C-A/T-S-D/A-S-N-A-V/T-S/--S--G/A-T-D/A-R/Q-N/G-M/F-P/T-A/G-L/M-T/A-A-G-T/S-L/V-P-A/Q-R/E-F-A-P-S/A-E/Q-C-R (SEQ ID NO:11). Exemplary peptides contain the sequence identified as SEQ ID NOS: 1 and 2.

The invention further includes a method of hardening glass, by coating an external surface of the glass with a synthetic pilin peptide containing a disulfide loop derived from the C-terminal receptor binding protein of Type IV *P. aeruginosa* (T4P) pilin and containing 0-10, preferably 0-5 additional residues on either or both the N- or C-terminal side of the loop. The pilin peptides may have the amino acid forms and preferred sequences noted above.

Also disclosed is a method of method of reducing the friction between elements in a machine that are in moving contact with one another, by coating the contacting surfaces of the elements with a synthetic pilin peptide containing a disulfide loop derived from the C-terminal receptor binding protein of Type IV *P. aeruginosa* (T4P) pilin, (ii) and 0-10, preferably 0-5, additional residues on either or both the N- or C-terminal side of the loop. The pilin peptide may have the amino acid forms and preferred sequences noted above.

In another aspect, the invention includes a bone implant comprising a metal implant structure, e.g., titanium or stainless steel structure, a portion of which is adapted to be placed within or against a region of bone, and carried on this portion, a coating of a bone-morphogenic peptide comprising a conjugate of a synthetic pilin peptide containing a disulfide loop derived from the C-terminal receptor binding protein of Type IV *P. aeruginosa* (T4P) pilin and containing 0-10, preferably 0-5, additional residues on either or both the N- or C-terminal side of the loop, and a bone-morphogenic.

For use as a joint replacement implant, the coated portion is adapted to be placed within the cortical region of bone, the conjugate may be a covalent conjugate of the pilin peptide and a bone morphogenic factor, which may be selected from the group consisting of RGD and bone morphogenic factors BMP2-BMP7.

For use as a dental implant, the coated portion may include an implant stem adapted to be placed within a hole formed in bone of the upper or lower jaw, and the conjugate may be a covalent conjugate of the pilin peptide and bone morphogenic factor, which may be selected from the group consisting of RGD and bone morphogenic factors BMP2-BMP7.

Also disclosed is an intravascular stent containing a expandable substrate, e.g., a stainless steel, titanium, or chromium substrate carrying on outer surface regions thereof, a coating of a synthetic pilin peptide containing a disulfide loop derived from the C-terminal receptor binding protein of Type IV *P. aeruginosa* (T4P) pilin peptide and containing 0-10, preferably 0-5 additional residues on either or both the N- or C-terminal side of the loop. The stent may be further coated with a drug-release coating containing an anti-restenosis compound.

In still another aspect, the invention includes a method of inhibiting an inflammatory response against a medical device inserted or implanted in a subject, by coating exposed surfaces of the device, comprising, prior to implantation, with a synthetic pilin peptide containing a disulfide loop derived from the C-terminal receptor binding protein of Type IV *P. aeruginosa* (T4P) pilin, (ii) and 0-10, preferably 0-5 additional residues on either or both the N- or C-terminal side of the loop, and composed of D-amino acids, a mixture of D- and L-amino acids, or D-amino acids in a retro-inverso (RI) form.

In a related aspect, the invention includes a medical device having surfaces that are exposed to inflammatory-response cells when implanted in a body, in which such surfaces are coated with a synthetic pilin peptide containing (i) a disulfide loop derived from the C-terminal receptor binding protein of Type IV *P. aeruginosa* (T4P) pilin, (ii) 0-10, preferably 0-5, additional residues on either or both the N- or C-terminal side of the loop, and (iii) composed of D-amino acids, mixture of D- and L-amino acids, or D-amino acids in a retro-inverso (RI) form. The exposed surfaces may be stainless steel, tin, iron, or titanium surfaces In a still further aspect, the invention includes a method of obtaining a polypeptide of interest, by the steps of (i) contacting a solid support formed of a material selected from the group consisting of stainless steel, tin, iron, titanium, chromium, plastic, glass, silicate, ceramics, and a mixture thereof with a composition containing a fusion polypeptide comprising the polypeptide of interest linked, at its N- or C-terminus through a cleavable linker to a synthetic pilin peptide containing a disulfide loop derived from the C-terminal receptor binding protein of Type IV *P. aeruginosa* (T4P) pilin and containing 0-10, preferably 0-5 additional residues on either or both the N- or C-terminal side of the loop, (ii) by this contacting, attaching the fusion protein to the solid substrate, (iii) washing the solid support to remove non-bound components in the composition, (iv) treating the washed solid support with an agent effective to cleave the linker in the fusion protein, thereby to release the polypeptide of interest in intact form from the solid support, and (v) separating the released polypeptide of interest from the solid support. The pilin peptide may have the amino acid forms and preferred sequences noted above.

The linker in the fusion protein may include an amino acid sequence that renders the linker susceptible to cleavage by a selected proteolytic enzyme, and treating step (iv) may include incubating the solid support in the presence of the selected proteolytic enzyme.

These and other objects and features of the invention will become more fully apparent when the following detailed description of the invention is read in conjunction with the accompanying drawings.

BRIEF DESCRIPTION OF THE DRAWINGS

FIGS. 1A-1D show the sequences of C-terminal receptor binding domains of Type IV *P. aeruginosa* (T4P) pilin in a number of bacterial genus/species/strains;

FIGS. 6A and 6B show the results of nano-indentation tests conducted at 20 μN (6A) and 50 μN (6B) loads;

FIGS. 7A and 7B are plots of displacement measurements at increasing loads for peptide coated (PAO in 7A and K122-4 in 7B) and uncoated stainless steel;

FIGS. 8A and 8B are conductance AFM surface maps of current flow between an uncoated (8A) and T4 P17 pilin peptide coated (8B) stainless steel substrate and an AFM tip;

FIG. 11 shows that the corrosion inhibitory effect of pilin peptide binding to a metal surface can be reversed when the pilin peptide is conjugated to another peptide, in this case, a leucine-zipper type E coil or an E/K coiled coil;

FIGS. 12A-12C are photographs showing the visual effects of corrosion on stainless steel samples that are either uncoated (12B), coated with a pilin peptide (12A), or coated with a pilin peptide having an coiled-coil duplex attached to the pilin (12C);

DETAILED DESCRIPTION

I. Definitions

Figure 2A:
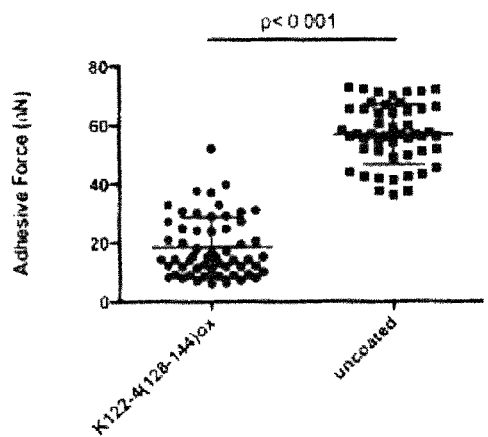
FIGS. 2A and 2B are plots showing adhesive force measurements made on uncoated stainless steel or stainless steel coated with K122-4 (2A) and PAO (2B) pilin peptide.

A "pilus" is a hairlike appendage found on the surface of many bacteria.

A pilin is the general term for the protein subunit of a pilus.

"Type IV *P. aeruqinosa* (T4P) pilin" refers to the pilus structures that *P. aeruginosa* bacteria use to generate motile forces, by adhering the distal end of the pilus to a biotic or abiotic surface, and contracting the pilus to pull the bacteria forward. All Type IV *P. aeruginosa* (T4P) pili contain a C-terminal receptor binding region that, in oxidized form, contain a disulfide loop of that can be classified into either a 12-residue loop or a 17-residue loop. FIG. 1 shows the disulfide loop region in a number of bacterial species whose C-terminal pilin regions has been sequenced.

A "disulfide loop derived from the C-terminal receptor binding protein of Type IV *P. aeruqinosa* (T4P) pilin" refers to a disulfide loop whose amino acid sequence corresponds to a known bacterial disulfide loop amino acid sequence, such as the *Pseudomonas* aeroginosa, strain PAK sequence identified by SEQ ID NO:4, or one of the sequences formed as a permutation one or more amino acid variations in the disulfide loop sequences between two or more different bacterial species and/or strains, such as one of the sequences contained in SEQ ID NO: 10 which is formed as a composite of the disulfide loop sequences of the four *P. aeruginosa* strains PAK, PAO, PA82935, and K-122-4.

A "synthetic peptide" refers to a peptide that is formed by solid-phase or recombinant peptide synthesis.

"A substrate formed of stainless steel, tin, iron, or titanium" means a metal substrate formed of stainless steel, tin, iron, or titanium or mixtures of two or more of these metals, or a metal or non-metal substrate coated with stainless steel, tin, iron, or titanium or a mixture thereof. The substrate may contain minor proportions of other metals, particularly transition metals from rows 4-6 and columns 9-12 of the period table, including cobalt, nickel, copper, zinc, ruthenium, rhodium, palladium, silver, cadmium, osmium, platinum, gold, chromium (present in stainless steel), and mercury.

"Covalent attachment of a T4P pilin peptide to a metal substrate formed of stainless steel, tin, iron, or titanium" means that the pilin peptide is attached to the metal surface through a bond that (i) resists displacement by free pilin peptides, and (ii) has an altered electron work function (EWF) indicating a change in the surface e⁻ orbitals of the material. Covalent attachment of a pilin peptide to such a metal substrate may also be characterized by a (i) change in surface adhesive force, (ii) change in surface hardness, (iii) change in conductance, and/or (iv) change in binding-energy peaks seen in X-ray photoelectron spectroscopy (XPS).

"Metal substrate with covalently bound compound" means a stainless steel, tin, iron, or titanium" substrate having a T4P pilin peptide covalently bound to the substrate surface, and a compound other than another portion of a pilin protein covalently bound, either directly or indirectly, to the pilin peptide. A compound is indirectly covalently bound to the T4P pilin peptide when it is linked to the pilin peptide through a high-affinity binding pair, such as a coiled-coil leucine-zipper pair, a biotin-avidin pair, or the like, where one of the members of the pair is covalently linked to the pilin peptide and the other, covalently linked to the compound.

"Exposed grain-boundary regions" of a metal substrate refer to surface regions of the substrate at which grain boundaries occur, that is, at the interface of two polycrystalline orientations of the metal atoms forming the substrate.

"Preferential localization of a pilin peptide at exposed grain boundary regions" means that the pilin peptide, and any compound covalently attached to the pilin peptide, has a greater concentration of molecules and/or thickness of surface coating at grain boundary regions than at exposed surface regions between grain boundaries.

II. Pilin Peptides

FIGS. 1A-1D show the sequences for the C-terminal pilin peptide regions containing a disulfide loop for a variety of bacterial genus/species/strains for which sequence information is available. The sequences given include the disulfide loop sequence (beginning and ending with a cysteine residue (C) and including in some cases up to five or more residues on either side of the loop. The single-letter amino acid designations are according to standard convention. In the normal oxidized form of the peptides, the peptides contain a disulfide bridge between cysteine residues.

The synthetic peptide employed in the present invention includes or is derived from one or more of the sequences shown in FIGS. 1A-1D. Where the sequence includes one of the sequences shown, it may include that disulfide loop alone, or the loop may additionally include up to ten, preferably five or fewer residues at either or both of the N-terminal or C-terminal side of the loop, where the additional non-loop residues typically include or are derived from one or more of the adjacent non-loop sequences. More generally, the sequences of both loop and non-loop regions may be derived from two or more sequences by aligning the sequences, preferably sequences having the same or nearly the same number of residues in the disulfide loop. For example, in FIG. 1A, four the peptides, corresponding to *P. aeruginosa* strains PAO (SEQ ID NO: 3), PAK (SEQ ID NO:4), PA82935 (SEQ ID NO:7), and K122-4 (SEQ ID NO:9) contain 14-mer disulfide loops. By aligning the disulfide loop sequences from the four *P. aeruginosa* strains in FIG. 1A, a combined sequence K/A/S/T-C-T/K/A-S/T-D/T/N-Q/V/A-D/E-E/IP/A/N-Q/M/K-F/Y-I/T/R/L-P-K/N-G/T--C-S/D/T/Q/N-K/N/D/T (SEQ ID NO:10) emerges. This 17-residue peptide (also referred to generically as T4P17) includes 14 disulfide loop residues, a single upstream (N-terminal side) non-loop residue and two downstream non-loop residues. Exemplary sequences within this sequences include the actual four different sequences from which SEQ ID:10 is derived, i.e., the sequences corresponding to the PAK (SEQ ID NO:3), PAO (SEQ ID NO: 4), PA82935, (SEQ ID NO:7), and K-122-4 (SEQ ID NO: 9).

As another example, the two *P. aeruginosa* strains G7-09 (SEQ ID NO:1) and PA110594 (SEQ ID NO:2), form a composite sequence S/T-I-D-W-G/A-C-A/T-S-D/A-S-N-A-V/T-S/--S--G/A-T-D/A-R/Q-N/G-M/F-P/T-A/G-L/M-T/A-A-G-T/S-L/v-P-A/Q-R/E-F-A-P-S/A-E/Q-C-R (SEQ ID NO:21)

Once a pilin peptide sequence is selected, it can be synthesized by standard recombinant or solid-phase synthesis. *E. coli* PAK(128-144)ox, for example, was expressed recombinantly from a pRLD-E plasmid, where the PAK(128-144)ox DNA sequence was spliced in-frame with the E-coil utilizing synthetic oligonucleotides and expressed in *E. coli* strain BL-21 according to known techniques (see, for example, Giltner et al., Mol. Microbiology. (2006) 59(4):1083 and references cited therein). The expressed peptide was purified by metal affinity chromatography, the purity and formation of the disulfide bridge was confirmed by mass-spectroscopy and N-terminal protein sequencing.

In one embodiment, the pilin peptides employed in the invention are formed of L-amino acids, i.e., amino acids having the natural L-isomer form. Pilin peptides composed of all L-amino acids can be formed both by conventional recombinant and solid-phase synthetic methods.

In another embodiment, the pilin peptides are composed of D-amino acids or mixtures of D- and L-amino acids. One purpose of including D-amino acids in the pilin peptide is to increase the peptide's resistance to proteolysis by one or more protease enzymes to which the peptide may be exposed. For example, *Pseudomonas* bacteria have a collection of proteases, including elastase, metallo proteases, and classic trypsin-like serine proteases, that require or target lysine and/or arginine residues in peptide cleavage. Thus, the pilin peptide could be synthesized to contain D-lysines, for example, at. K136 and K140 in the K122-4 pilin peptide. Preferably, in making the peptide resistant to as many proteases as possible, the pilin peptide should be formed entirely from D-amino acids. Pilin peptides composed of all D-amino acids or a mixture of D- and L-amino acids can be formed by conventional solid-phase methods utilizing activated D- or L-form amino acid reagents in the synthesis. (See, for example, Guichard, G., et al., Proc. Nat. Acad. Sci. USA Vol. 91, pp. 9765-9769, October 1994)

In still another embodiment, the pilin peptides are composed of D-amino acids synthesized in a reverse-sequence direction, that is, in a carboxy to amine end direction, to produce a so-called retro-inverso (RI) pilin peptide. Retro-inverso (RI) form pilin peptides also have the advantage of greater resistance to proteases, and are thus advantageous in the applications described herein where the pilin-coated material is exposed to proteases, e.g., in a biological setting, or in an environment subject to bacterial growth. Methods for synthesizing RI-form peptides are detailed, for example, in Fletcher, M. D. and Campbell, M. M., Partially Modified Retro-Inverso Peptides: Development, Synthesis, and Conformational Behavior, Chem Rev, 1998, 98:763-795, which is incorporated herein by reference.

III. Treating Metal Surfaces

The invention includes, in one aspect, an improved method for treating stainless steel, tin, iron, or titanium metal material having surfaces with exposed grain boundary regions, to reduce the rate of corrosion of the material. The method may be used separately or in combination with one of a number of other anti-corrosion methods, such as passivation. The metal material may have a single exposed surface with grain-boundary regions, or a number of external surfaces to be treated, or contain pores or internal reticulations which are accessible from the external surface(s) of the material. As will be appreciated, the method is suitable to treating any stainless steel, tin, iron, or titanium metal material that is subject to chemical corrosion, e.g., in an oxidative atmosphere or by contact with corrosive liquids, such as basic or acidic liquids.

In practicing the method, the metal material may be first washed one or more times, e.g., in an ethanol bath, to remove contaminants. The material is then contacted with a solution of the pilin under conditions effective to covalently bind the pilin to the exposed surfaces of the material. In a typical treatment method, the material is placed in a solution of pilin peptide at a peptide concentration between 2 µg/mL and 50 µg/mL pilin, e.g., 10 µg/mL, in an aqueous buffer, e.g., phosphate buffered saline, at a near-neutral pH, e.g., pH 7, and contacted with the solution for a period, e.g., 5-120 minutes, until a suitable coating of pilin peptides has formed.

Alternatively, the material to be coated may be sprayed with a pilin solution, and contacted with the sprayed solution in a high-humidity environment over a desired contact time, e.g., 5-120 minutes.

In still another embodiment, a pilin coating is applied to selected areas of the metal surface, e.g., in a microfabrication operation, or to selectively apply the peptide to exposed grain-boundary regions on the material. In this embodiment, a solution of the peptide is delivered to the exposed surface(s) of the material in an area-specific manner, e.g., by an ink-jet printer or the like.

IIIA. Treatment Method and Changes in Metal Surface Properties

This section describes exemplary methods for treating a metal surface to enhance its corrosion resistance, and studies conducted in support of the invention that demonstrate, in addition to increased corrosion resistance, (i) reduced adhesive force of the treated surface, (ii) altered electron work function of the treated surface, (iii) increased hardness of the treated surface, (iv) reduced conductance, and (v) coating stability over a period of at least two months.

Sample Preparation

Commercial grade 304 2B finish plates (20 gauge) stainless steel sheets 1 mm thick were cut into samples with dimensions of 1 cm×1 cm. Samples were annealed at 1140° C. for 1 hour in air and cooled in air. The surface was polished using sand papers of 120, 240, 320, 400, 600, and 800# grit, followed by a final polish with 1200# grit paper.

Aluminum and stainless steel samples with dimensions of 1 cm×1 cm×1 cm were polished using the polishing protocol described previously. Neither of these samples were annealed prior to polishing.

Coating Samples with Peptide or Monomeric Pili

Stainless steel and aluminum samples were washed using a commercial dishwashing soap for 1 minute followed by rinsing with distilled water. Samples were then immersed in 95% ethanol with gentle agitation for 15 minutes, rinsed with distilled water, and immersed in reagent grade acetone for 1 minute. Samples were rinsed 5 times with distilled water and allowed to air dry. Samples were immersed in a phosphate buffered saline (PBS) solution containing 10 µg/mL of peptide or monomeric pili and were incubated at room temperature (RT) for 1 hour with gentle agitation. The solution was removed and samples were washed 6 times with distilled water and allowed to air dry.

Carbon steel samples were cleaned using the protocol described above, but were instead rinsed with 100% methanol following the acetone washing step and immediately immersed in 100% methanol to prevent rapid air corrosion that results when exposed to water. Peptide was dissolved in 100% methanol and a final concentration of 10 µg/mL was used to immerse the carbon steel sample. Samples were incubated at RT for 1 hour with gentle agitation. Samples were washed 6× with 100% methanol and allowed to air dry.

Adhesive Force Measurements

The adhesive force between a standard Au-coated AFM silicon nitride tip with a tip radius of 50-70 nm and a peptide-coated surface was measured using an atomic force microscope (AFM). To determine the adhesive force between the AFM tip and the coated surface the AFM was used in "contact" mode. The tip was approached to the surface, allowed to make contact, and the deflection of the cantilever when the tip is pulled away from the surface was measured. The total amount of deflection, which reflects the adhesive force, was detected by laser beam. The adhesive force can be determined quantitatively from the beam deflection if the spring constant of the cantilever is known. In this study, the cantilever spring constant was 0.06 N/m. For each experiment, between 20 and 50 adhesive force measurements were obtained per sample.

Figure 2B:
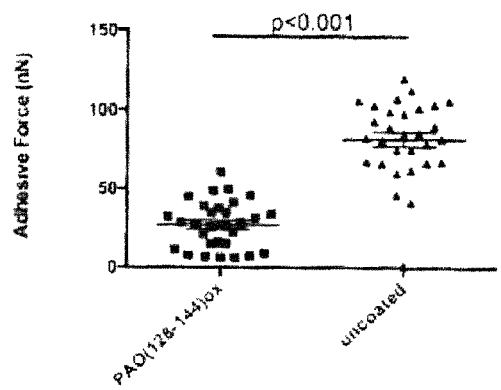

The results of the adhesion study with stainless steel samples coated with either K122-4 or PAO pilin peptide are plotted in FIGS. 2A and 2B, respectively. As seen in FIG. 2A, the adhesive force for the coated metal clustered in a range between about 5-40 nN (nanoNewtons), with an average around 20 nN, compared with an uncoated sample, where the adhesive force clustered between about 40-75 nN, with an average around 60 nN. Similar results were obtained with the PAO pilin coating. Since adhesive force is a reflection of electron activity, e.g., Van de Walls interactions, it can be concluded that the peptide coating serves to mask the metal surface electron layer.

Similar adhesion measurements on peptide-coated aluminum plates showed virtually no difference in the adhesion force between coated and uncoated plates.

Work Function Measurements

The electron work function (EWF) of coated and uncoated stainless steel samples was measured conventionally with a SKP370 Scanning Kelvin Probe. The technique operates using a vibrating capacitance probe, and through a swept backing potential, the work function difference is measured between the scanning probe reference tip and sample surface. The samples investigated were like those used in the adhesion studies, except that a sample coated with PAK pilin peptide was also examined.

Figure 3A:
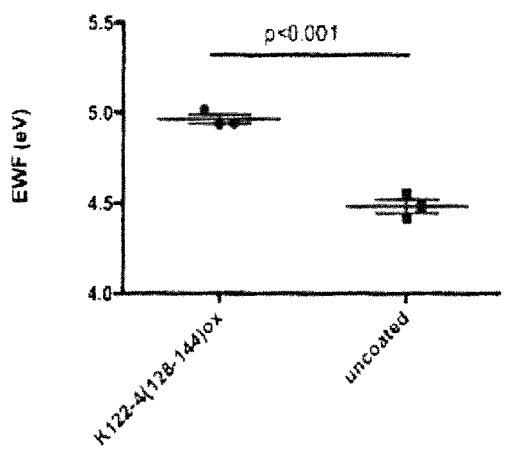
FIGS. 3A and 3B are plots showing electron work functions (EWF) for uncoated stainless steel and stainless steel coated with K122-4 (3A) and PAK (3B) pilin peptide.
Figure 3B:
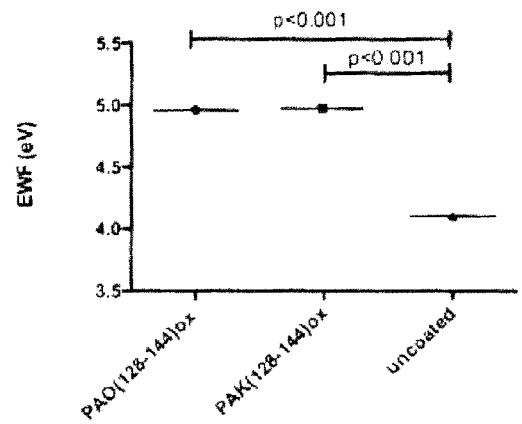

The results of the study are plotted in FIG. 3A for uncoated and K122-4 pilin peptide coated samples, and in FIG. 3B, for uncoated and PAO- and PAK pilin peptide coated samples. For all three coating, the pilin peptide coating elevated the surface EWF by at least about 0.5 eV, to a final value of about 5 eV.

Similar EWF measurements on peptide-coated aluminum plates showed virtually no difference in the EWF between coated and uncoated plates.

Stability of the Peptide Coating

Figure 4:
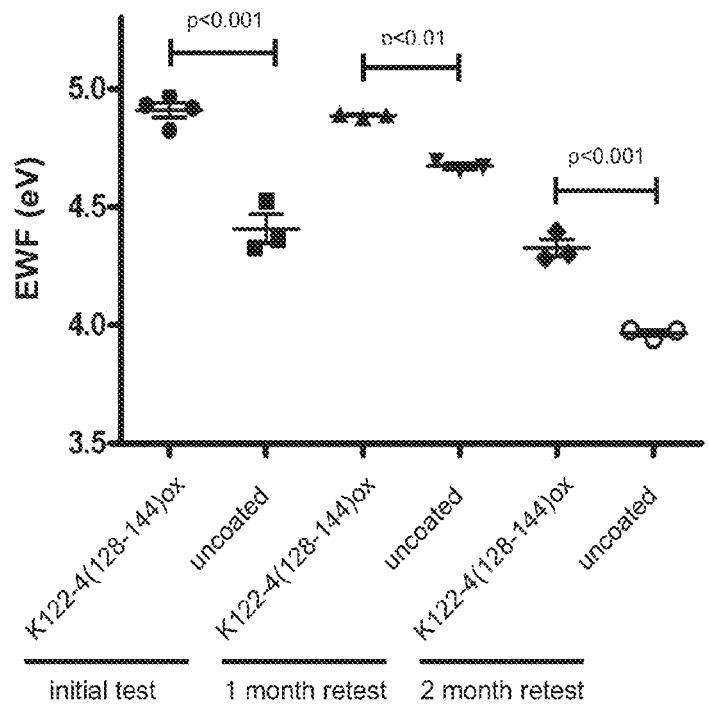
FIG. 4 shows EWF measurements with coated and uncoated stainless steel taken over a two-month period.

FIG. 4 shows the results of measurements on the K122-4 pilin peptide-coated sample taken over a 2-month time period after coating. The greater EFW of the coated sample with respect to the uncoated slide was observed over the two-month study period, indicating a coating stability of at least two months.

Nanoindentation/Hardness

A triboscope (Hysitron, Minneapolis, USA) was used to examine the changes in the mechanical properties of peptide-coated samples. The triboscope is a combination of a nanomechanical probe and an AFM. The probe, a diamond pyramidal Vickers indenter, has a nominal radius of 150 nm with a force sensitivity of 100 nN and a displacement resolution of 0.2 nm. During nanoindentation, a force-depth curve is obtained for each indentation and the total depth displacement of the tip into the surface of the sample was obtained from this curve. Nanoindentation tests were performed using forces of 50 to 800 μN. Five force-depth curves were obtained for each force load.

Figure 5:
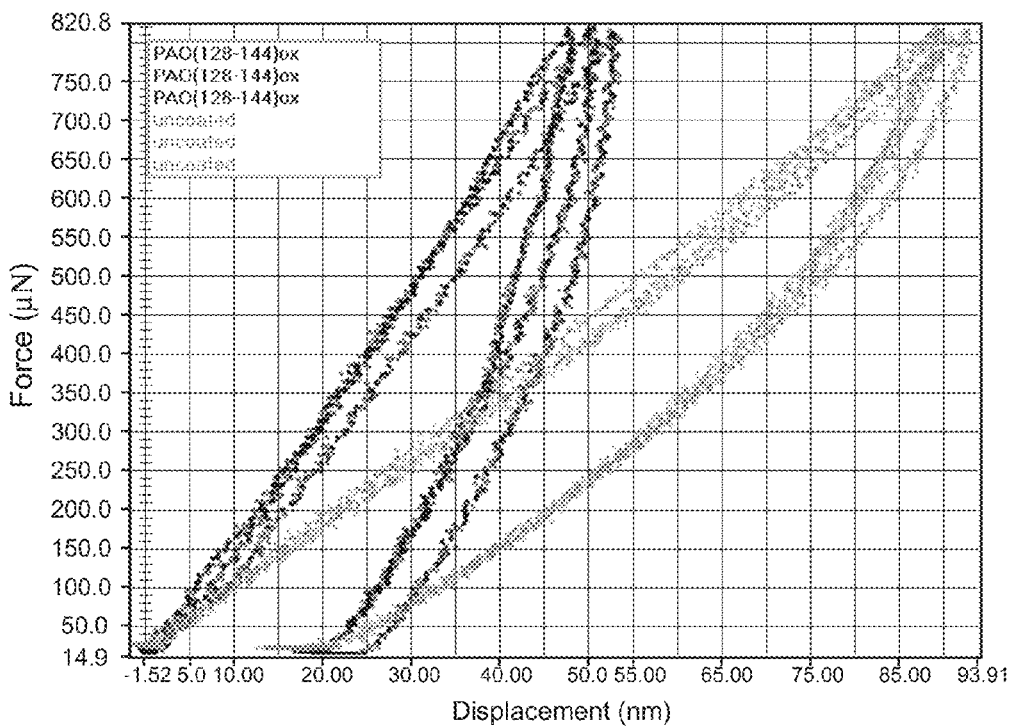
FIG. 5 shows a force-displacement curve of peptide-coated and uncoated stainless steel under a 800 nM load.

The force-displacement curves of peptide-coated (dark) and uncoated (light) stainless steel under a range of loads between 50 and 800 μN are shown in FIG. 5. Total displacement at the 800 μN load is shown at the top of the graph, and is in the range 45-55 nm for the coated slide and is between about 90-95 nm for the uncoated slide. Based on this test, the coated slide has nearly twice the hardness as the uncoated slide. More generally, the coating is effective to increase the hardness of a stainless steel, tin, iron, or titanium metal surface by at least about 20%, preferably at least about 30%, and up to 50% or more.

FIGS. 6A and 6B plot displacements with nanoindentations produced at 20 μN (6A), and 50 μN (6B) for coated and uncoated slides. Consistent with the data from FIG. 5, coated slides had a hardness of between about 20%-100% greater than the uncoated slides.

The same type of study is plotted in FIGS. 7A and 7B for PAO-coated (7A) and K122-4 coated (7B) over a force range of 50-800 μN (7A) and 50-400 μN (7B), with substantially the same results. In both cases, the pilin peptide coated nearly doubled the surface hardness of the metal sample.

Similar nanoindentation tests on peptide-coated aluminum plates showed virtually no change in surface hardness between coated uncoated plates.

Increased Conductance

Conductance is a measure of the ability of a material to conduct current flow. One standard method for measuring surface conductance uses an atomic force microscope (AFM) to measure the electrical current that flows from a specific location on the surface to the AFM tip under a specified low-voltage potential bias. The AFM displays the current flow (in pA) between the surface and the tip quantitatively as a specific color, represented by different shades of gray in FIGS. 8A and 8B for uncoated and pilin-coated stainless steel plates, respectively. In general, darker to lighter shades indicates greater to smaller currents (between 28.0 to 24.5 pA). From the two figures it is observed that surface regions of the uncoated stainless steel sample in FIG. 8A are quite variable over the sample surface and has predominant dark shading indicating a relatively high current flow, whereas the surface regions in the pilin coated sample in FIG. 8B are predominantly low conductance and substantially more uniform in conductance profile. The results are consistent with the EFW data from FIGS. 3A and 3B, showing substantially higher metal work function (a measure of the work needed to extract a surface electron) in the pilin-coated material.

Corrosion Resistance

Figure 9A:
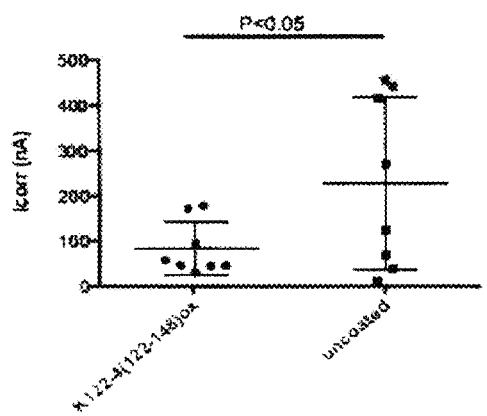
FIGS. 9A-9B are measurements of corrosion characteristics in coated and uncoated stainless surfaces, showing that pilin-coated stainless steel has a corrosion current (Icorr) that is significantly below that for uncoated stainless steel (9A), that pilin-coated and uncoated stainless steel do not have significantly different corrosion potentials (Ecorr) (9B)

There are a number of techniques available for investigating corrosion resistance or susceptibility to corrosion in a material surface. One method is to measure the current across a metal plate at a fixed potential. The measured current reflects the surface electrons to shuttle between redox forms, with a higher current indicating a greater potential for corrosion. The plot in FIG. 9A shows the measured current (Icorr) for 304 2B finish plates (20 gauge) stainless steel sheets prepared as above, either uncoated or coated with K-122-4 pilin peptide. The results show a significantly lower Icorr for the coated plates, indicating greater corrosion resistance.

Figure 9B:
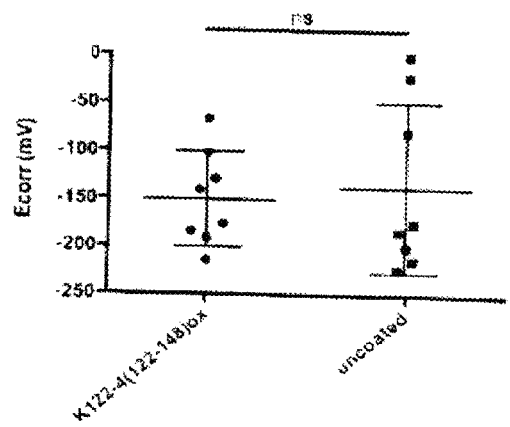

It can be asked whether the difference in Icorr observed in the above study is related to the potential (Ecorr) at which current first begins to flow across the metal surface. This question was investigated by looking at the potential (Ecorr) at which current in the metal first begins to flow. The results of the study, shown in FIG. 9B, indicate that both the coated and uncoated metal samples have similar Ecorr values, indicating that the differences in Icorr values seen in FIG. 9A are not due to differences in the voltage potential response between the two samples.

Figure 10A:
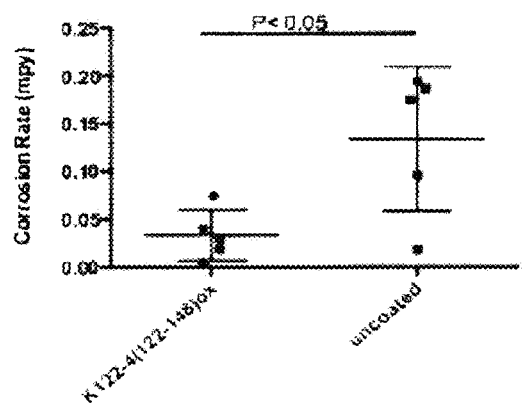
FIGS. 10A and 10B are plots showing that pilin-coated stainless steel has a significantly lower corrosion rate than uncoated stainless steel (10A) and a significantly higher resistance to polarization compared to uncoated stainless steel (10B)

Corrosion rate measurements, measured in mills (milli-inches)/year (mpy) for the K-122-4 coated and uncoated samples are plotted in FIG. 10A. The results are consistent with the differences in Icorr seen in FIG. 9A. In particular, the pilin peptide coating appears to reduce corrosion rate over threefold, when average rates are compared.

Figure 10B:
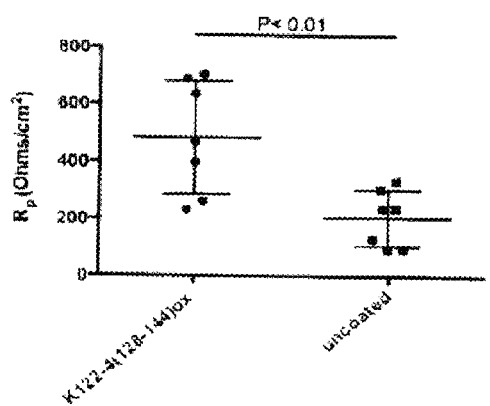

Another widely used technique in corrosion monitoring is polarization resistance, defined as the slope of the potential current density curve at the free corrosion potential, yielding a resistance value Rp that can be related to corrosion current by a known mathematical relationship. FIG. 10B plots the Rp values for coated and uncoated stainless steel values, showing that the peptide coating significantly enhances Rp as a measure of corrosion resistance.

Interestingly, the effect of the pilin peptide in inhibiting corrosion can be reversed when the pilin is conjugated to another peptide having a strong dipole and/or high charge density, in this case, a leucine-zipper type E coil, or the same E coil having bound thereto, an oppositely charged K coil in an E coil/K coil pair. As seen in FIG. 11, the corrosion rate for the uncoated stainless steel sample is substantially lower than that sample having bound pilin in a pilin-E or E/K coil form.

The visual effect of corrosion testing on the various stainless steel samples discussed above is seen in FIGS. 12A-12C. In this study, samples were either uncoated (12B) or coated with a pilin peptide (12A) or a pilin peptide conjugated to an E/K coiled coil pair. In each case, the sample was subjected to previously described corrosion testing in a weak salt solution. The pilin-coated plate shows very little surface corrosion compared with the uncoated plate, while the pilin-conjugate coating appears to significantly enhance corrosion.

In summary, coating a metal such as stainless steel, tin, iron, or titanium with a synthetic pilin peptide containing a disulfide loop derived from the C-terminal receptor binding protein of Type IV *P. aeruginosa* (T4P) pilin and containing 0-10, preferably 0-5 additional residues on either or both the N- or C-terminal side of the loop, is effective to increase both the hardness and corrosion resistance of the metal surface. The increased corrosion resistance is evidenced by an change, e.g., increase in the electron work function of the metal surface by at least 0.2 EFW units, as well as the Icorr, corrosion rate, and Rp values described above The increased hardness is evidenced by the reduced nanoindentation produced striking the metal surface with the tip of an atomic force microscope with a given force by at least 20%.

Other metals contemplated in the method are transition metals from rows 4-6 and columns 9-12 of the period table, including cobalt, nickel, copper, zinc, ruthenium, rhodium, palladium, silver, cadmium, osmium, platinum, gold, and mercury, and mixtures and alloys thereof, and the metalloids silicon and germanium, and oxides thereof.

IIIB. Additional Evidence for Covalent Bonding of the Pilin Peptide to the Treated Metal The altered electron work function of a coated metal and the enhanced resistance to erosion indicate that the pilin peptide has altered the electronic properties of the coated surfaces, suggesting formation of a covalent bond between the peptide and metal that alters the free-electron orbitals of the metal. Additional support for this finding comes from the peptide displacement assay and X-ray photoelectron spectroscopy (XPS) study reported in this subsection.

Peptide/Pili Displacement Assay

One indicator of covalent interaction between a compound and substrate is the inability of the compound to be displaced from the substrate when the complex is incubated in the presence of the compound in solute form. Here, the ability of exogenous pilin peptide to displace pilin peptide bound to a stainless steel surface was investigated. Commercial grade 304 2B finish plates (20 gauge) stainless steel sheets 1 mm thick were cleaned as previously described. These sheets were not annealed or polished. The sheets were assembled into a 96-well Schleicher and Schuell Minifold TM System (Mandel Scientific). Fifty microliters of a solution containing 10 μg/mL of biotinylated PAK peptide or biotinylated purified pili were added to wells (5 replicates) and the manifold was incubated at RT for 1 hour with gentle agitation. Wells were washed six times with 1×PBS. Unlabeled PAK peptide was added to replicate wells in increasing amounts (0 to 10 μg/mL) and the steel manifold was incubated 1 hour at RT with gentle agitation. Wells were subsequently washed six times with PBS. Displacement of the bound biotinylated peptide or pili was assessed using streptavidin-horseradish peroxidase (HRP). Strepavidin-HRP (Sigma) was diluted 1/500, 100 μL were added per well, and the manifold was incubated for 1 hour at RT. One hundred and fifty microliter of developing buffer (0.01 M sodium citrate buffer pH 4.2 containing 1 mM 2,2'-Azino-bis-(3-ethylbenzthiazoline-6-sulfonic acid) diammonium salt (ABTS) (Sigma) and 0.03% (v/v) hydrogen peroxide) were added per well. The manifolds were incubated at RT for 10 min with gentle agitation. The reaction solution was transferred to a 96 well flat-bottomed micro titer place (Corning) and the absorbance at 405 nm was determined using a FLUOstar OPTIMA plate reader (BMG LABTECH).

Figure 13:
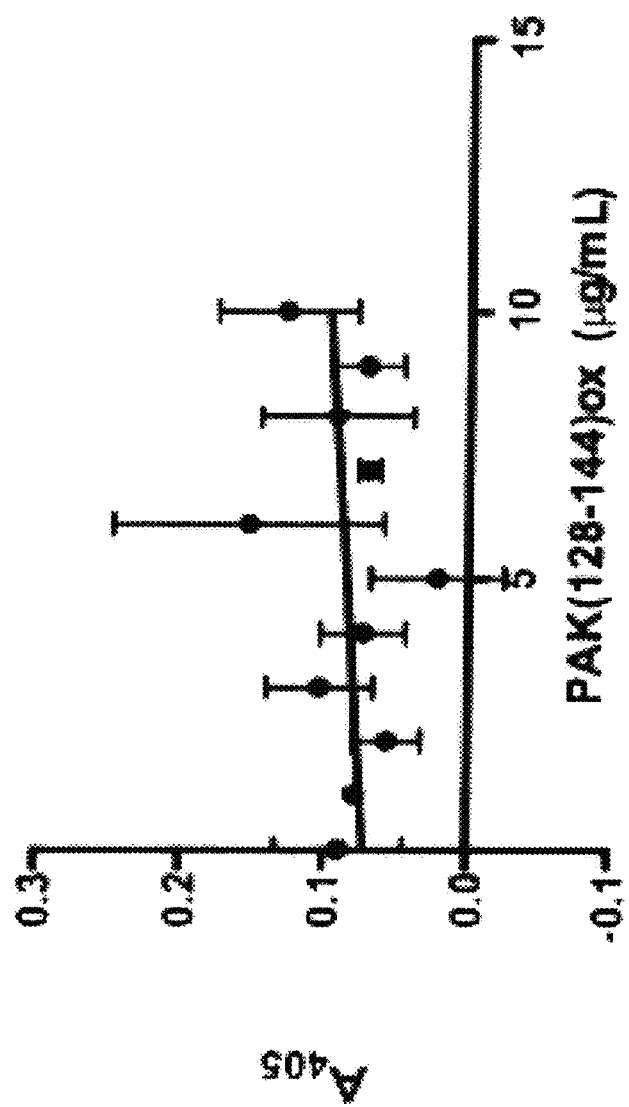
FIG. 13 shows that bound pilin peptide is not displaced from stainless steel surfaces in a competitive binding assay employing increasing amounts of exogenous peptide.

As seen from the data plotted in FIG. 13, there was no measurable loss of bound pilin peptide from the metal surface, even at relatively high concentrations of soluble pilin peptide, demonstrating that the bound pilin peptide is in equilibrium with unbound peptide, indicating a covalent bond attachment between the peptide and metal surface. Further evidence of the covalent bonding of the peptide to the metal surface is provided by the corrosion resistance studies below.

XPS Characteristics

X-ray photoelectron spectroscopy (XPS) is a quantitative spectroscopic technique that measures the elemental composition and electronic state of the elements that exist within a material. XPS spectra are obtained by irradiating a material with a beam of X-rays while simultaneously measuring the kinetic energy and number of electrons that escape from the top 1 to 10 nm of the material being analyzed. XPS requires ultra high vacuum (UHV) conditions.

Figure 14:
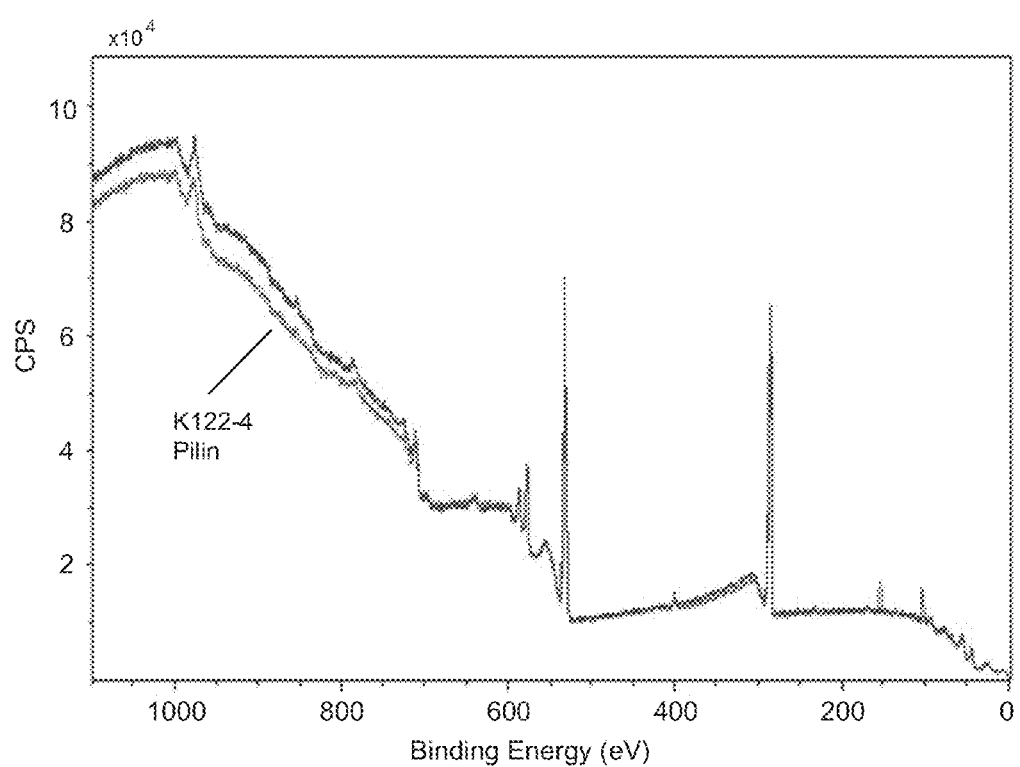
FIG. 14 is a XPS plot of an uncoated and K-122-4 pilin peptide coated stainless steel sample.

An Axis-165 Spectrometer (Kratos Analytical) was used to examine the photo-emitted electrons from an uncoated and pilin-coated samples. The spectra for emitted electrons from the two samples are shown in FIG. 14. As seen, the pilin-coated sample contains two unique peaks with binding energies around 100 and 150 eV that are not present in the uncoated sample. One possibility is that the two peaks represent sulfur-metal bonds that are substantially red shifted because of conjugated electron bonding. There is no evidence of N or O bonding with the metal, suggesting that the likely covalent (shared electron) bond interaction with the between the pilin and metal is with one or both of the two sulfur atoms in the pilin peptide.

IIIC. Grain Boundary Effects

A grain boundary is the interface between two grains, or crystallites, in a polycrystalline material. Grain boundaries are defects in the crystal structure, and tend to decrease the electrical and thermal conductivity of the material. The high interfacial energy and relatively weak bonding in most grain boundaries often makes them preferred sites for the onset of corrosion and for the precipitation of new phases from the solid.

Since a grain boundary can serve as an initial site for corrosion, it was of interest to determine whether pilin peptide binding to a metal surface occurred preferentially at grain boundary sites. To investigate this question, the adhesive force studies described above using a pilin-peptide coated AFM tip were further refined to investigate adhesive force effects within a grain and at a grain boundary. The "test" and "control" surfaces in the study were stainless steel plates coated with a PAO pilin peptide or a peptide having a scrambled sequence of the PAO amino acids. For each sample, the adhesive force within a grain and at a grain boundary was measured.

As seen from the results given in Table 1 below, the pilin peptide had an adhesive force about 20 nN lower than the same material with the scrambled sequence within a grain boundary, and a an adhesive force about 43 nN lower at a grain boundary. The results indicate either that the pilin peptide is localizing preferentially at the grain boundary, i.e., the peptide has a greater coating thickness at the grain boundary, or that the same level of pilin binding produces a greater adhesive force effect at a grain boundary. In either case, the data may explain the magnitude of the anti-corrosion effect seen by binding a pilin peptide to a metal surface.

TABLE 1

Grain boundary region contributions to adhesive force.

| AFM Tip | Competitor | Adhesive Force Within Grain (nN) | Adhesive Force at Grain Boundary (nN) | Fold Increase at Grain Boundary |
|---|---|---|---|---|
| Coiled-coil-PAK (128-144)ox | PAO (128-144)ox | 39.5 ± 9.4 | 44.5 ± 11.6 | 1.13 |
| Coiled-coil-PAK (128-144)ox | PAO (128-144)ox_Scrambled | 59.7 ± 8.4 | 87.5 ± 14.2 | 1.47 |
| Attributable to PAK (128-144)ox | | 20.2 ± 17.9 | 43.0 ± 25.8 | 2.12 |

IIID. Pilin Peptide Binding by D- and RI-Forms of Pilin

To examine the ability of D- and RI-forms of pilin peptide to bind to a metal (stainless steel) sample, and the characteristics of the pilin-coated materials, D- and RI forms of the K122-4 pilin peptide were synthesized and tested against the L form of the same plin peptide. Stainless steel plates were coated with either the L-form pilin peptide (three different batches), the D-form pilin, or RI-form pilin, and one plate was uncoated.

Figure 15A:
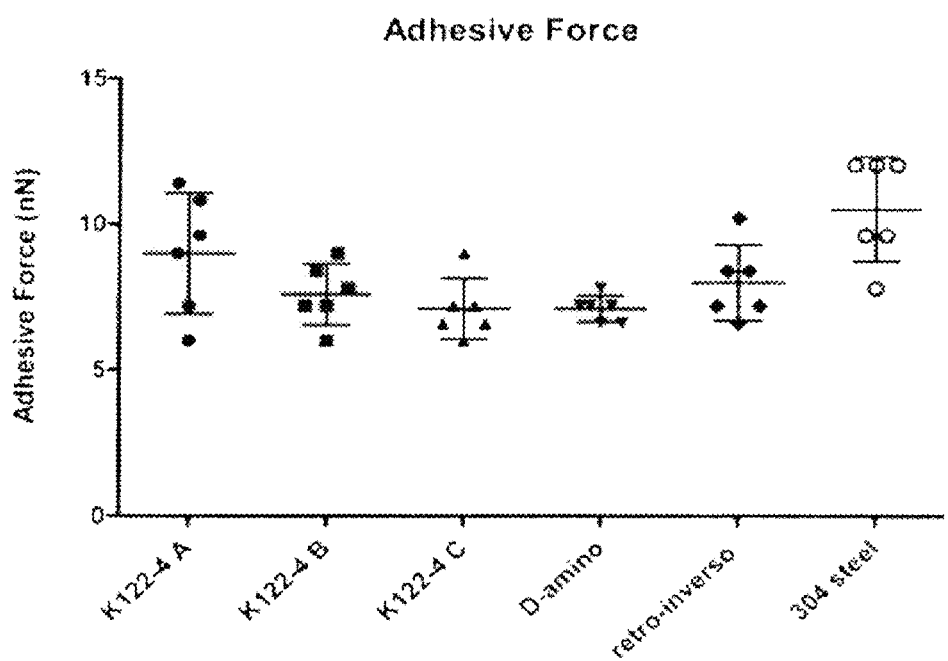
FIGS. 15A and 15B show adhesive force measurements on a stainless steel sample coated with both L- and D-forms or pilin peptides (15A) and the EWF force measurements on a stainless steel sample also coated with the same L- and D-forms of pilin peptides (15B)

The plates were first examined for changes in adhesive force, similar to the study reported above with respect to FIGS. 2A and 2B. As seen in FIG. 15A, substantial reductions in adhesive force were seen for all three forms of the pilin peptide relative to the uncoated plate.

Figure 15B:
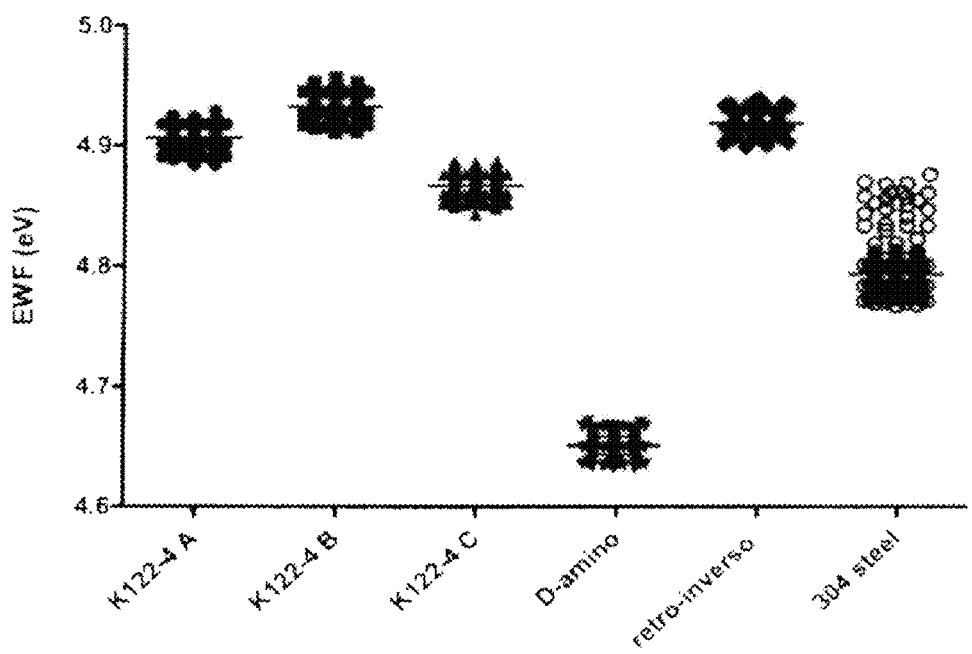

EWF measurements on the same six samples, conducted as described above with respect to FIGS. 3A-3B, are plotted in FIG. 15B. Interestingly, the D-amino acid form gave a substantially lower EWF than any of the other five plates, including the uncoated plate, whereas the RI-form gave EWF values comparable or higher than the L-form pilin samples.

The results indicate that both D- and RI-forms of a pilin peptide are able to interact with a stainless steel plate in a manner that alters the electronic properties of the metal surface.

Figure 16A:
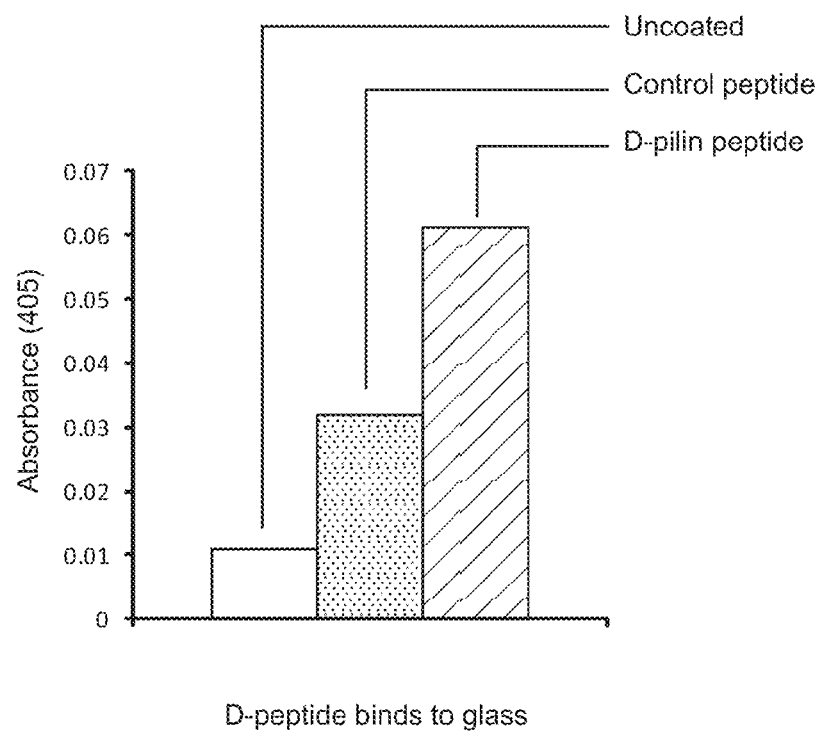
FIGS. 16A and 16B demonstrate the ability of pilin peptide (D-form) to bind tightly to a stainless steel coronary stent (16B) and to a glass surface (16A).

The ability of the D-form pilin to bind tightly to stainless steel was investigated by comparing peptide binding to a stainless steel stent that was either uncoated, coated with a biotinylated control peptide (either a scrambled or a non-binding regions of a pilin sequence), or coated with a biotinylated D-form pilin peptide. The amount of peptide bound to each stent surface was measured by first washing the surface of a 3% solution of SDS at 37° C., followed by several more washes in PBS. The washed surfaces were incubated with streptavidin-HRP (horse radish peroxidase), then exposed to an ABTS substrate, and the absorbance read at 405 nm. As seen in FIG. 16A, about twice as much D-form pilin peptide bound to the stainless steel stent as did the control peptide.

To investigate the resistance to enzyme proteolysis of a metal-bound D-form pilin peptide, relative to a metal-bound L-form pilin peptide, stainless steel plates were coated in duplicate with the L-form peptide, D-form peptide, and control (scrambled pilin sequence). One sample from each duplicate was then incubated with trypsin, at a concentration of 0.25%, EDTA 1 mM, pH 7.4 at 37° C. for 60 minutes. Thereafter the samples were assayed for bound protein by the HRT assay method described above.

Figure 17A:
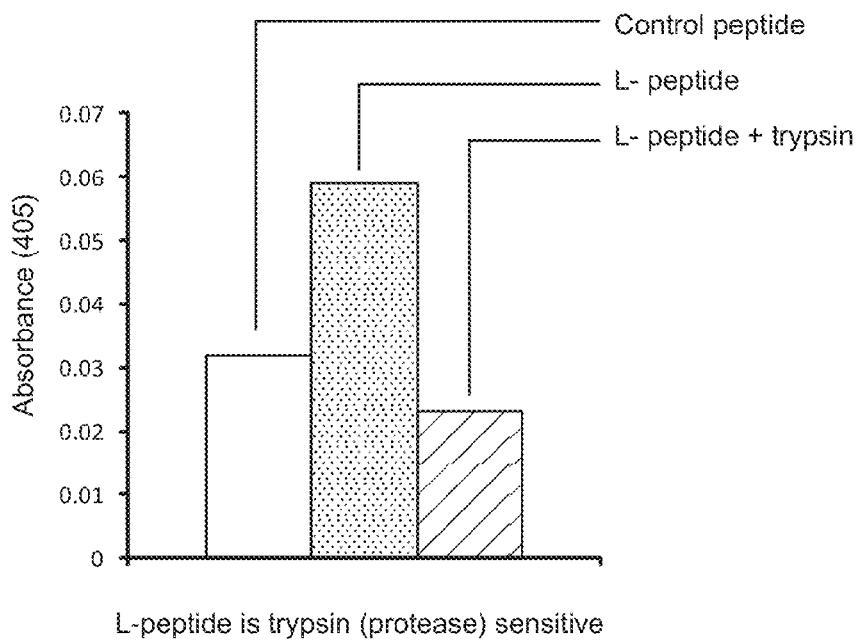
FIGS. 17A and 17B are bar graphs showing the relative resistance to protease digestion in L-amino acid and D-amino acid pilin bonded to a stainless steel sample.
Figure 17B:
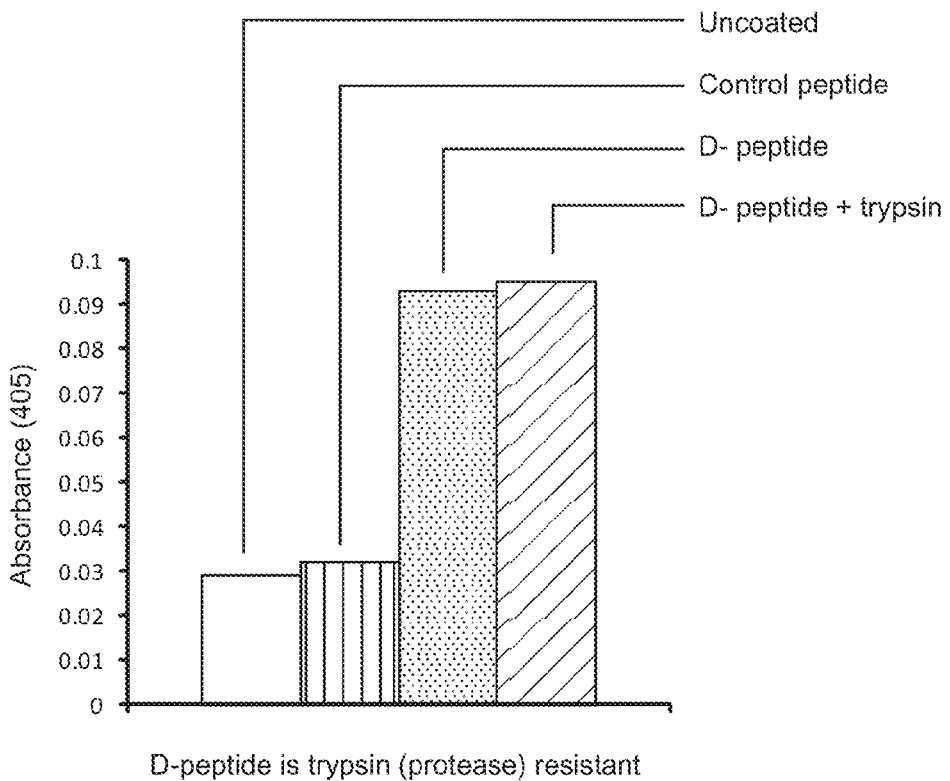

FIG. 17A shows bound peptide levels for the L-form pilin before and after exposure to trypsin. As seen, more than half the pilin peptide was removed by the protease treatment. By contrast, the amount of bound D-form pilin peptide was substantially unaffected by protease digestion (FIG. 17B). The results demonstrate that (i) the covalent binding of an L-form peptide to stainless steel does not confer protection against protease digestion, and (ii) the bound D-form pilin peptide is substantially protected against enzyme proteolysis.

IIIE. Related Applications

Figure 16B:
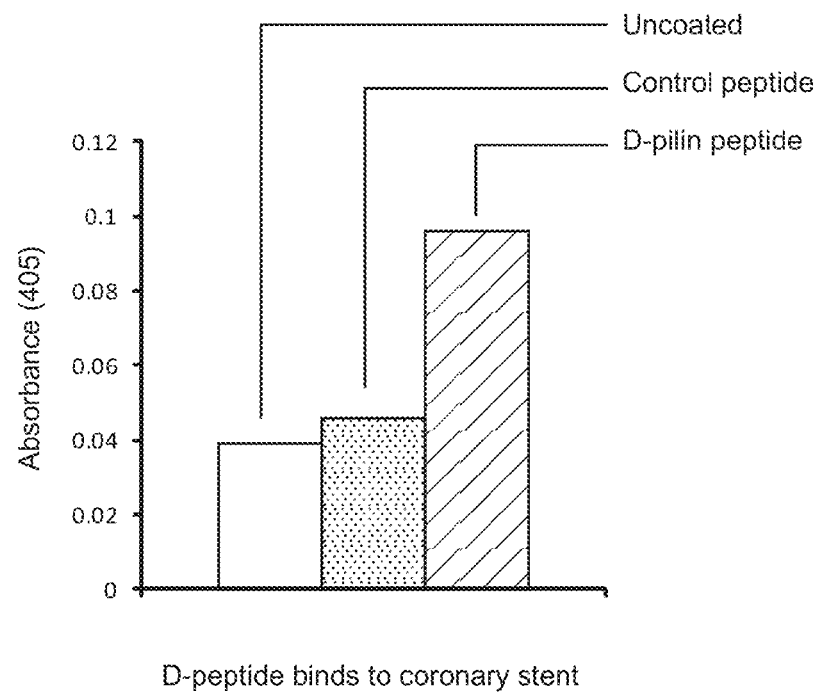

The ability of pilin peptide binding to increase the hardness of the coated material can also be exploited, in accordance with another aspect of the invention, to surface harden other materials, such as plate glass or automobile safety glass. In this application, a cleaned glass surface is contacted with the pilin peptide under conditions effective to coat the surface with a layer of the pilin. The amount of protein bound to the substrate was measured as above, using an HRP assay. As seen in FIG. 16B, the D-form peptide was tightly bound to the glass surface, resisting removal even by SDS treatment, and about twice as much pilin peptide bound to the stainless steel stent as did the control peptide.

In another application, the surface treatment is used to enhance the lubricity of coated metal surfaces that are in moving contact with one another in a machine. Here the target machine components are pretreated for enhanced surface lubricity by exposing the parts to a pilin peptide, as above, under conditions to form a covalently attached pilin coating. Alternatively, a solution of the pilin peptide may be applied to contacting surfaces of the machine during operation or during temporary shutdown, to maintain the greater lubricity of the machine components during machine operation.

IV. Coated Metal Substrate and a Biosensor Device

This section considers applications of the present invention to diagnostic devices in which an analyte-specific target compound, e.g., a receptor, is attached to a detection surface through a pilin peptide in accordance with the invention. Where the detection surface is a metal to which the pilin peptide covalently bonds, through electronic interactions with the metal surface, the device may function in an electronic biosensor mode, as described below.

IVA. Metal Substrate with Covalently Bound Compound

This aspect of the invention includes a metal substrate to which a compound, e.g., receptor, is covalently attached at the substrate surface by means of (i) covalent attachment of a pilin peptide to the substrate, as detailed above, and direct or indirect covalent attachment of the compound to the pilin, i.e., through a pilin-compound conjugate. The coated substrate is formed either by first attaching an unconjugated pilin peptide to the metal surface, followed by covalently linking the compound to the bound pilin, or by first forming the pilin-compound conjugate, followed by binding the conjugate to the metal surface, as described above for an unconjugated pilin peptide. Methods for covalently attaching a compound to the pilin peptide, e.g., by direct chemical coupling through amine or carboxyl groups, or using bifunctional coupling reagents, are well known. Where the compound is itself a peptide, the pilin-compound conjugate can be formed as a fusion protein, by recombinant or solid-phase synthesis. The coated substrate has altered surface electronic properties by virtue of the pilin binding to the metal surface, and studies conducted in support of the invention, detailed below, show that current flow across the substrate surface is modulated by binding of an analyte-related molecule to the surface-bound compound, making it possible to record such binding events by a change in current flow across the substrate. As will be seen below, the compound may also be covalently attached indirectly to the substrate, e.g., through an E/K coiled-coil complex.

IVB. Biosensor Device with Bound-Pilin Substrate

Figure 18A:
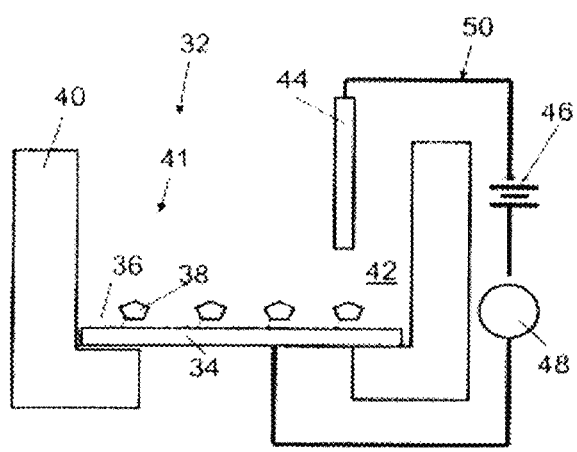
FIGS. 18A and 18B are schematic illustrations showing the operation of a biosensor device constructed according with one embodiment of the invention.
Figure 18B:
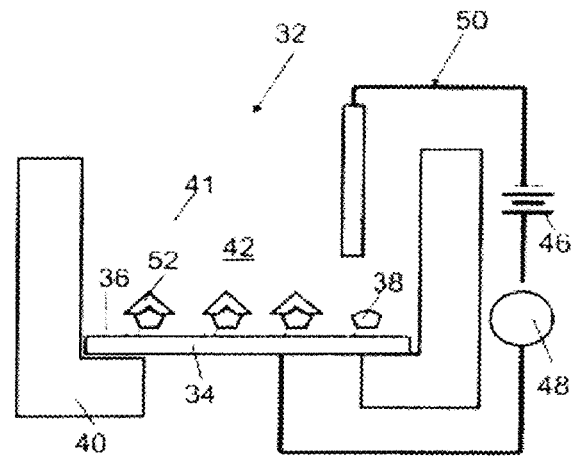
Figure 19:
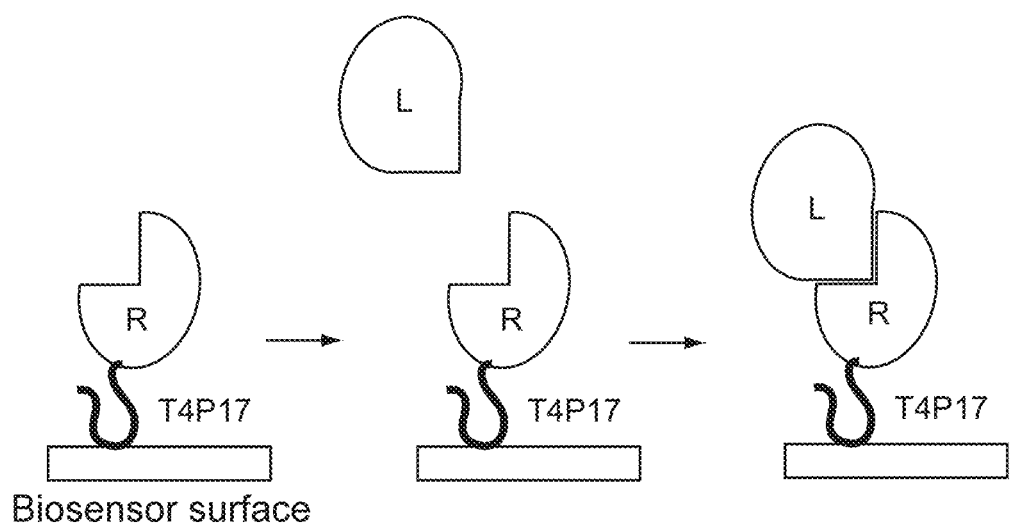
FIG. 19 illustrates analyte-binding steps in a biosensor in which the analyte-binding agent R is attached directly to the biosensor surface through a pilin peptide.
Figure 20:
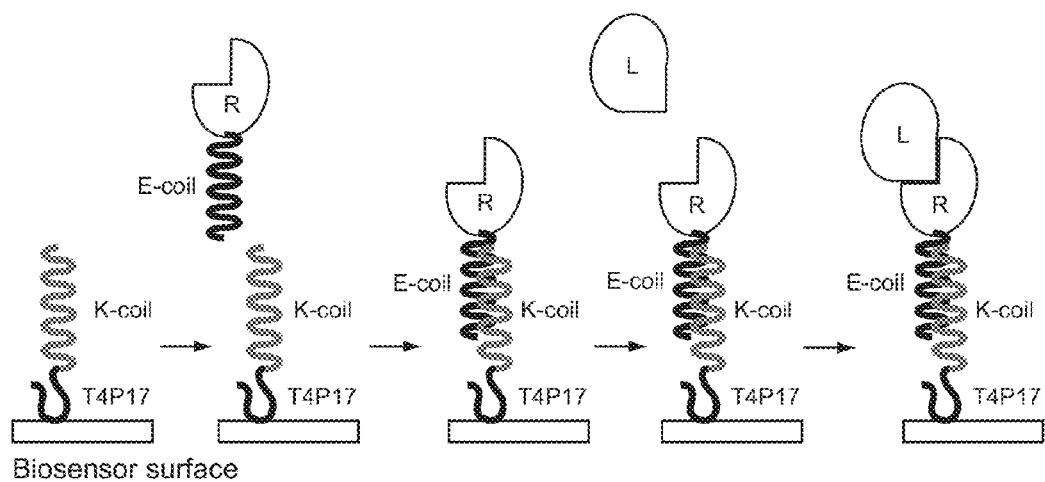
FIG. 20 illustrates analyte-binding steps in a biosensor in which the analyte-binding agent R is attached to the biosensor surface through a pilin peptide coiled-coil complex.
Figure 21:
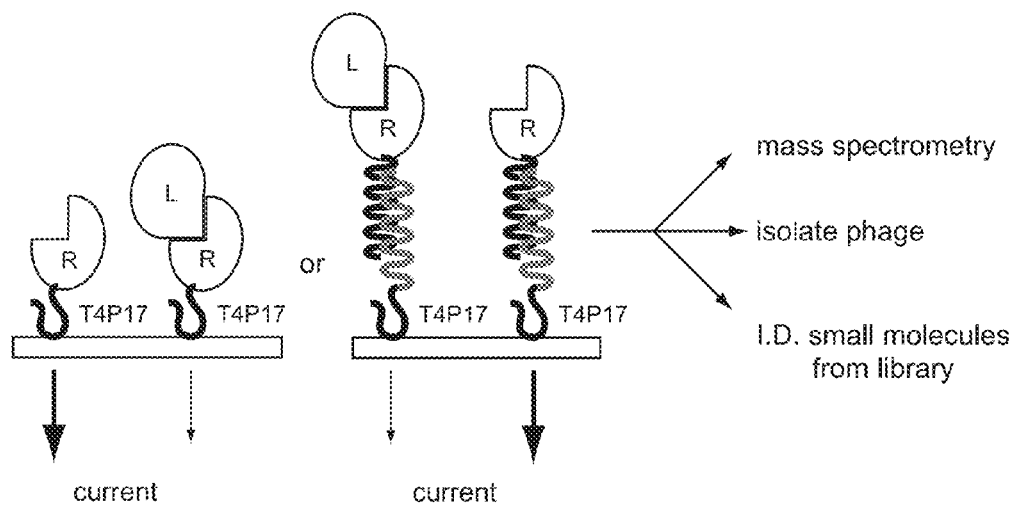
FIG. 21 shows different detection configurations in the biosensor of the invention.

FIGS. 18A and 18B illustrate a biosensors assay device 32 constructed in accordance with an embodiment of the invention. The device takes advantage of the altered electronic properties observed with a pilin-peptide coating on the metal detection plate 34. That is, plate 34 is formed of a metal such as stainless steel, tin, iron, or titanium, having altered electronic surface properties when coated by the pilin peptide. As above, the pilin coating is formed by exposing the plate surface with a conjugate of the above pilin peptide 36 and an analyte-binding moiety 38, or by attaching the compound to the bound, unconjugated pilin peptide. The plate itself forms the lower surface of a shallow biosensors reaction container 41 whose sides are formed by a wall 40 in the device, and which is partially filled with an aqueous conducting medium 42.

A biosensor circuit 50 in the device includes an electrode 44 which extends into the container, a voltage source 46 and an ammeter 48, where the opposite circuit connection is to the lower side of the detection plate.

FIGS. 19 and 20 illustrate two surface configurations of the biosensor. In FIG. 19, a receptor (ligand-binding) molecules (R) is covalently attached to a pilin peptide (hook shaped moiety) which in turn is covalently coupled to the biosensor surface. Conductance across the biosensor substrate is determined by (i) the bonding interaction of the pilin peptide with the substrate surface, and (ii) the effect of receptor R on conductance. When a ligand L, e.g., an analyte, binds to the receptor, the electronic properties at the surface are further modulated, causing a shift in observed biosensor current. The current shift indicated in FIG. 21 is from higher to lower current after ligand binding to the receptor.

In FIG. 20, the receptor R is coupled indirectly to the substrate surface through covalent bonding of a pilin/K coil conjugate to the substrate surface, followed by a coiled-coil interaction with a receptor-E coil conjugate. In this embodiment, the conjugate forming the biosensor surface coating is a three-component conjugate of the pilin peptide and a K coil, an E coil conjugated to the a receptor R and a ligand L which can bind to the R. In this embodiment, the biosensor is first reacted with analyte, to bind analyte to the coating, masking K-coil sites on the surface. This reaction may be read directly as a change in current caused by the masking of the K-coil, or an E-coil reagent may be added at this stage to bind to the E-coil in proportion to the amount of K-coil still unmasked after the analyte reaction.

Figure 22A:
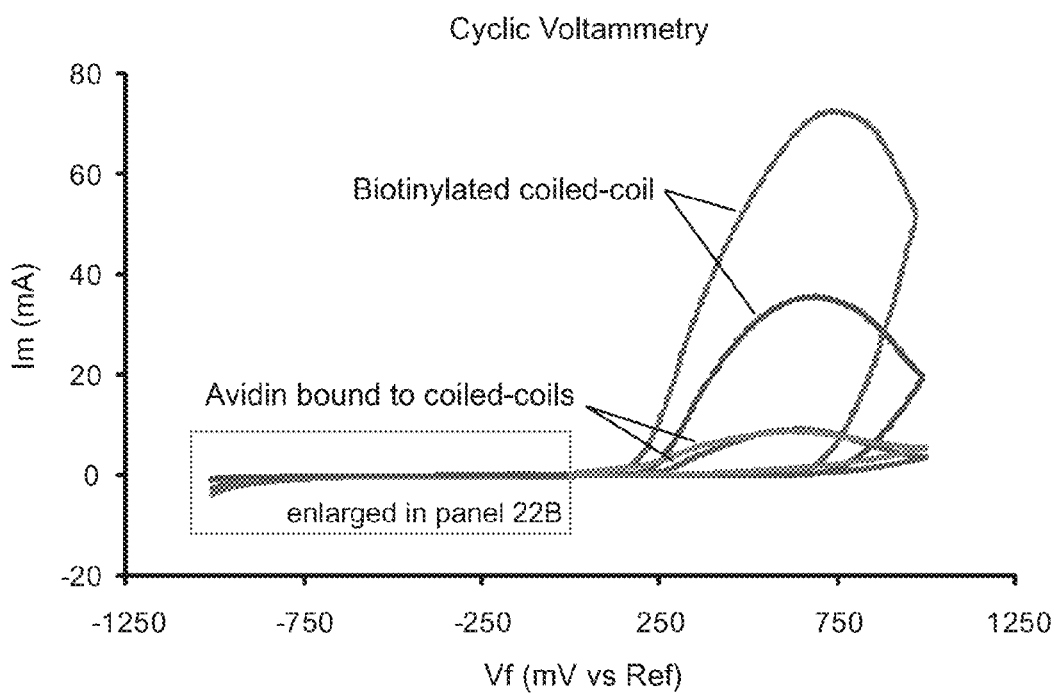
FIGS. 22A and 22B are cyclic voltammetry plots recorded in a biosensor device before and after binding analyte binding to the receptor, where 22B is an enlargement of the rectangular panel in FIG. 22A.
Figure 22B:
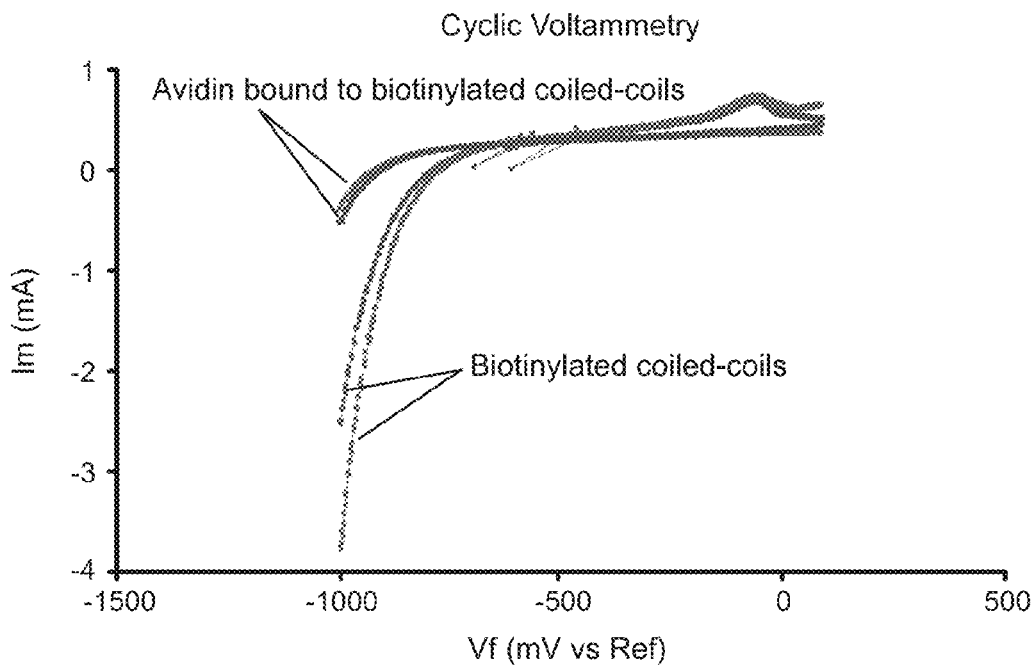

FIGS. 22A and 22B are voltameter cycle curves for a biosensor interaction in which a His moiety (the receptor) is bound to the substrate surface through the coiled-coil configuration illustrated in FIG. 20. FIG. 22A shows the complete cyclic voltammetry curve for the His moiety displayed on a K-coil complexed to an E-coil covalently linked to stainless steel via the pilin construct by itself and following the addition of an anti-His antibody specific for the His moiety. FIG. 22B shows an amplification of the left hand portion cyclic voltammetry curve demonstrating that current flow is altered by antibody binding to the His moiety not only under a positive voltage bias but also in a negative voltage bias. Binding of an anti-His antibody to the His receptor produces the lowermost current cycle, evidencing a drop in current flow with "analyte" binding to the biosensor surface. Similar results were obtained when the His receptor was bound directly to the biosensor surface through a pilin peptide, and the analyte employed was an anti-His antibody.

To understand the operation of operation of the sensor, it is useful to consider the corrosion resistance data from Table 2 below, which show Icorr, Ecorr, Corrosion Rate, and Rp data for (i) an uncoated stainless steel plate (Unmodified) (ii) a stainless steel plate coated with a pilin peptide conjugated to an E-coil (negatively charged leucine zipper) peptide (E-PAK), and (iii) a third stainless steel plate coated with the same conjugate to which has been bound, the oppositely charged K-coil peptide, that is, the peptide is conjugated to an E-coil/K-coil heterodimer (K-E-PAK). Considering the Icorr column, the data show that E-PAK binding to the plate significantly increases its Icorr value, opposite the effect seen with the PAK pilin alone (see FIG. 9A). When the conjugate is neutralized (K-E-PAK), the Icorr value is now substantially less than the uncoated metal, similar to the effect observed for the unconjugated peptide. A similar effect on Ecorr, corrosion rate, and Rp values is seen from the data, namely, neutralizing the E-coil effect by binding with the oppositely charged K coil significantly alters the surface effect produced by the E-PAK pilin binding.

TABLE 2

Corrosion resistance data for pilin conjugates on stainless steel

| Icorr (nAmps) | Ecorr (mV) | Corrosion Rate (mpy) | Rp (Ohms/cm$^2$) | |
|---|---|---|---|---|
| E-PAK | 1940 | 87.2 | 0.1981 | 121.722 |
| K-E-PAK | 273 | 36.1 | 0.2492 | 130.145 |
| Unmodified | 802 | 4.2 | 0.0547 | 303.141 |

Various advantages of the biosensor can be appreciated from the above description. First, because the pilin peptide that covalently links the analyte-binding receptor to the biosensor surface directly affects the electronic active at the biosensor surface, altering the size and charge of the surface complex by ligand bind produces a direct effect, e.g., reduction, in current flow. Secondly, the interaction of molecules with metal surfaces is fundamentally different from the interaction with plastics, as electron activity or the ability of the surface electrons of the metal to interact directly with the molecule determines the degree and force of the interaction. Metals that do not form an oxide layer (such as gold) have very active surface electrons (due to edge effects of the crystals) and readily absorb materials to their surface. These materials are susceptible to the non-specific adsorption of proteins and other molecules from sample matrices and are therefore not useful as biosensor platforms. Metals such as stainless steel undergo surface oxidization to form a passive oxide layer (passivated), minimize non-specific binding events and do not readily bind materials to their surface (hence their widespread use in the medical and food industries). The ability to easily bind specific peptide/protein components to passivated stainless steel using the T4P17 peptide confers a significant advantage in improving the signal to noise ratio in detecting ligand-receptor interactions in biosensor applications. As stated above, T4P17 binding to stainless steel mediates electron transfer and can function as a biosensor when exposed to a voltage bias. The studies reported above demonstrate the ability to modulate electron flow across the biosensor surface in response to ligand binding to a pilin-receptor conjugate bound to the metal surface.

IVE. General Assay Device with Bound-Pilin Substrate

Figure 23A:
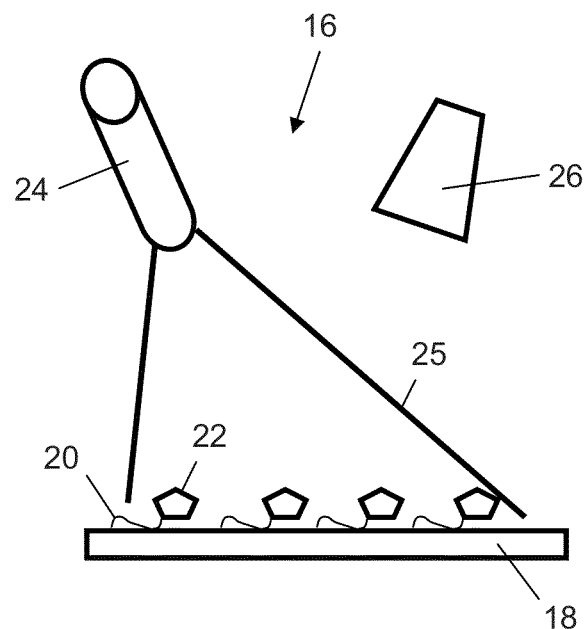
FIGS. 23A and 23B illustrate an analyte detection device constructed according to a more general embodiment of the invention.
Figure 23B:
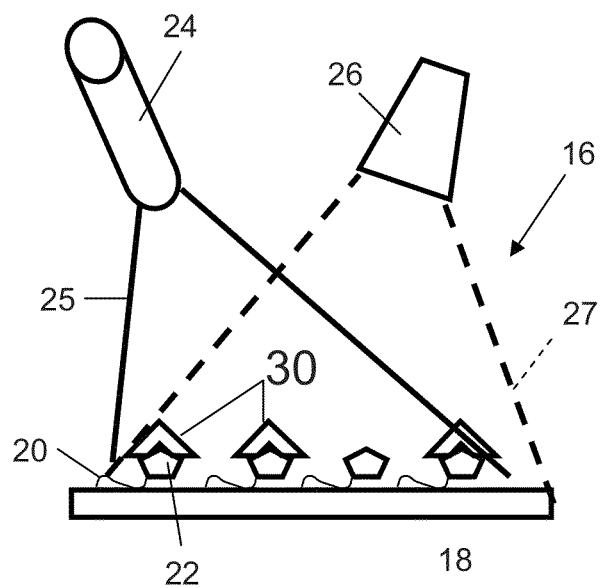

FIGS. 23A and 23B show an analyte-detection device 16 having a plate 18 whose upper detection surface is coated with a conjugate of a pilin peptide 20 and an analyte-specific target molecule 22. Although the plate may be formed of a variety of materials to which the pilin peptide binds. It is binds, it is preferably a metal, such as stainless steel, tin, iron, and titanium surface, to which the pilin binds covalently. The covalent binding provides a number of advantages in terms of ease of production, protein stability, coating stability. Also included in the device is a beam source 24, e.g., UV source, for irradiating the detection surface as shown at 25 and a photo-detector 26.

In operation, the surface of the detection plate is covered with a fluid sample containing an analyte of interest, shown in FIG. 23B as soluble analyte molecules 30, and these are allowed to react with analyte-specific molecules 22 on the detection surface. In the fluorescence detector shown, the reaction mixture may contain a fluorescent-labeled antibody or other binding agent capable of reacting specifically with the analyte bound to the detection surface. The detection surface is then washed to remove unbound components. The reaction surface is now assayed for the presence and level of bound fluorescence, as indicated in FIG. 23B, showing emitted fluorescence at 27, to complete the assay.

It will be appreciated that convenient fluorescence assays may be incorporated into the device. For example, the pilin peptide may contain a fluorescent moiety and the analyte-binding moiety may include a fluorescent quencher effective to quench fluorescence from the pilin fluorescent moiety. In this embodiment, binding of analyte to the analyte-binding moiety is effective to mask the effect of the quencher, producing greater fluorescence in the presence of analyte binding to the analyte-binding moiety.

In an alternative embodiment, the pilin peptide and analyte-binding moieties may include first and second fluorescent species, respectively, that are effective to produce fluorescence resonance energy transfer, when excited at a given excitation wavelength. In this configuration binding of the analyte to the analyte-binding species is effective to inhibit such energy transfer, reducing the observed fluorescence.

V. Medical Devices with Coated Metal Surfaces

The studies reported above on peptide binding to certain metal surface, e.g., stainless steel, tin, iron, and titanium surface, demonstrate that pilin peptide binding alters the surface electronic properties of the metal, indicating formation of a covalent (electron sharing) bond between the peptide and metal. This discovery provides a novel method for covalently attaching a bioactive molecule, e.g., peptide, lipid, nucleic acid, metabolite, or drug molecule, covalently to a stainless steel, tin, iron, and titanium surface, and novel medical devices having bioactive compounds covalently attached to an exposed device metal surface through a pilin peptide.

Other metals contemplated in the method are transition metals from rows 4-6 and columns 9-12 of the period table, including cobalt, nickel, copper, zinc, ruthenium, rhodium, palladium, silver, cadmium, osmium, platinum, gold, and mercury, and mixtures and alloys thereof, and the metalloids silicon and germanium, and oxides thereof.

In this method, the surface of the metal is contacted with a synthetic pilin peptide containing a disulfide loop derived from the C-terminal receptor binding protein of Type IV *P. aeruginosa* (T4P) pilin and containing 0-10, preferably 0-5 additional residues on either or both the N- or C-terminal side of the loop.

If the pilin peptide has been prepared in advance to include a covalently attached bioactive molecule, the contacting step alone results in the covalent attachment of the bioactive molecule to the metal surface. Methods for preparing conjugates of peptides (in this case, a pilin peptide) with bioactive molecules are well known and include forming a fusion protein between the peptide and a peptide bioactive molecule, and the use of specific chemical modification reactions to provide reaction sites for covalent attachment of the bioactive molecule to the peptide. For example, the final step in the solid-phase synthesis of the pilin peptide may include the addition of a reactive group, e.g., aldehyde, that can be used for covalent reaction with the bioactive molecule.

Alternatively, the bioactive molecule may be reacted with the pilin peptide after peptide attachment to the metal surface, again employing conventional bifunctional reagents or specific chemical-group reaction chemistry to couple the bioactive molecule covalently to the bound pilin on the metal surface.

Another application, for use in obtaining a polypeptide of interest, is carried out by first synthesizing a fusion protein containing a pilin peptide of the type described above with the polypeptide of interest, e.g., by recombinant polypeptide synthesis. The fusion protein is then contacted with a solid support formed of stainless steel, tin, iron, titanium, chromium, plastic, glass, silicate, ceramics, or a mixture thereof, thereby attaching to the fusion protein to the support through attachment of the pilin peptide moiety to the support.

After washing the support to remove unbound material, the support is treated with an agent capable of specifically cleaving the polypeptide of interest from the bound pilin peptide. This may involve treating the support with a proteolytic enzyme capable of specifically cleaving a defined-sequence linker in the fusion protein, or treating the support with a chemical or a radiation energy source capable of specific cleavage of the linker in the fusion protein. The released polypeptide of interest is then eluted or washed from the support in substantially purified form.

Another application of the binding method is in preparing implantable devices that have desired surface properties or carry desired bioactive molecules on their surfaces. For example, a bone implant in accordance with the invention will include a stainless steel or titanium implant structure, a portion of which is adapted to be placed within or against a region of bone. To accelerate bone attachment to the implant, this portion is coated with a conjugate of a synthetic pilin peptide of the described above and a bone-morphogenic factor, such as RGD or bone morphogenic factors BMP2-BMP7.

In a related application, the pilin peptide is applied to the surface of a metal or polymer stent, producing a stent in accordance with the invention that has improved surface properties, e.g., less tendency to promote surface reactions that can lead to undesired clotting or scarring at the intravascular implant site. The coating may alternatively be formed by a conjugate of a pilin peptide and a bioactive molecule, such as pilin-limus drug conjugate having a bioreleasable linker, e.g., ester linker between the pilin and drug.

As will be seen below, the coated metal surfaces significantly reduce inflammatory response that the body can amount against the device.

VI. Medical Devices with Reduced Inflammatory Response

In addition to inflammation mediated by infection or cellular injury/stress, a tremendous amount of iatrogenic inflammation is induced by medical instrumentation. The exposure of human tissues, cells, and proteins to non-biocompatible medical devices triggers dysfunctional host responses, the clinical effects of which are greatly underestimated. Examples include tissue reaction and dysfunctional wound healing following the insertion of medical prostheses including vascular grafts, artificial joints and other implantable devices. Similarly, the activation of leukocytes and the coagulation system results in significant morbidity in critically ill patients regularly exposed to extracorporeal circuits such as cardiopulmonary bypass and hemodialysis. These events further impact healing, regeneration and rehabilitation of patients with acute and chronic diseases.

According to another aspect of the invention, it has been discovered that the inflammatory response to certain metals used in medical devices, e.g., titanium, can be inhibited by coating the metal surfaces with pilin peptides formed of D-amino acids, a mixture of D- and L-amino acids, and D-amino acids in a retro-inverso (RI) form.

Figure 25A:
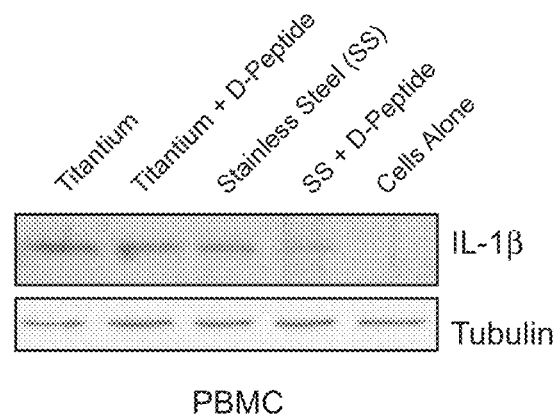
FIGS. 25A and 25B are a Western blot (25A) and bar graph plot (25B) showing the effect of D-pilin peptide coating on a PBMC immunological response to an uncoated and pilin-coated titanium or stainless steel surface.
Figure 25B:
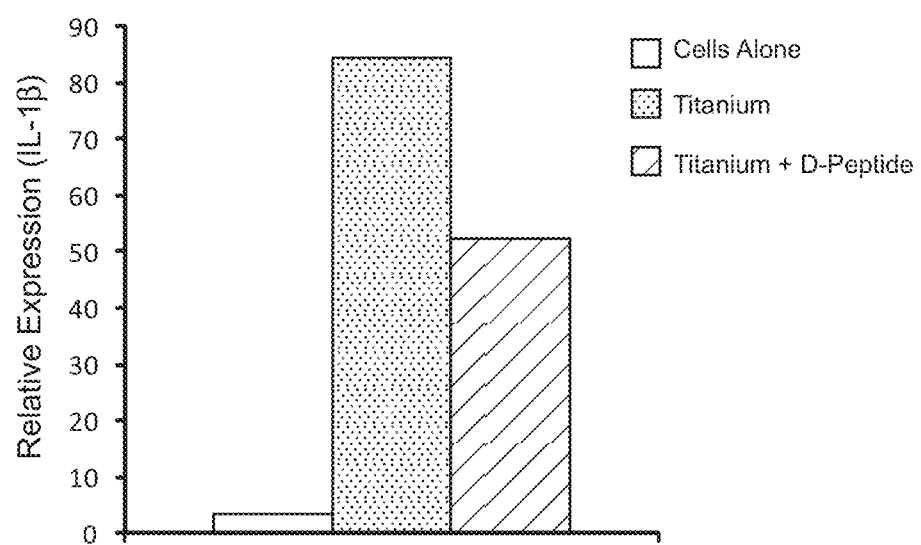

In one study, human peripheral blood mononuclear cells (PBMC) cells were incubated under standard cell-culture conditions either alone or in the presence of a titanium or steel plate, which was either uncoated or coated with the D-form pilin peptide. After 24 hours incubation in RPMI medium at 37° C., the culture medium was assayed for the cytokine IL-1β, which is an indicator of an inflammatory response in the PBMC. Tubulin was assayed as a housekeeping control. FIG. 25A shows Western blots for IL-1β and tubulin measured for each of the five samples. As seen, the D-form pilin peptide coating was effective to inhibit the inflammatory response in both the stainless steel and titanium samples. This effect can be seen quantitatively for the titanium sample in the bar graph shown in FIG. 25B.

Figure 26A:
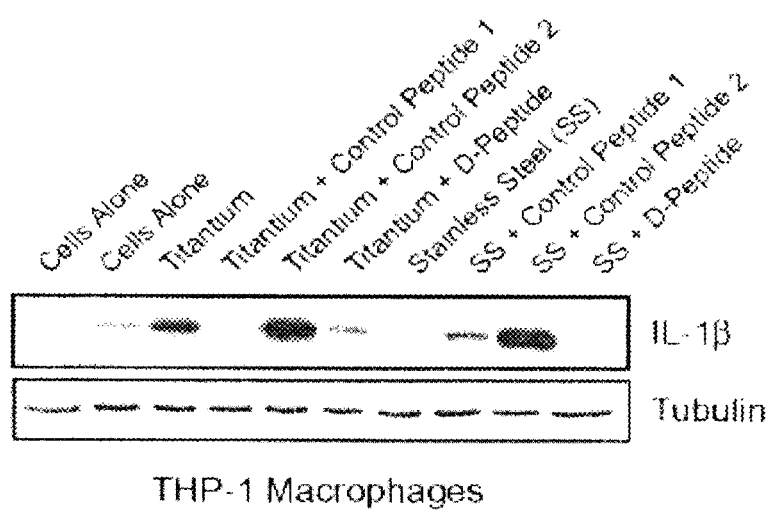
FIGS. 26A and 26B show a Western blot (26A) and bar graph plot (26B) showing the effect of D-pilin peptide coating on a human macrophage immunological response to an uncoated and pilin-coated titanium or stainless steel surface.
Figure 26B:
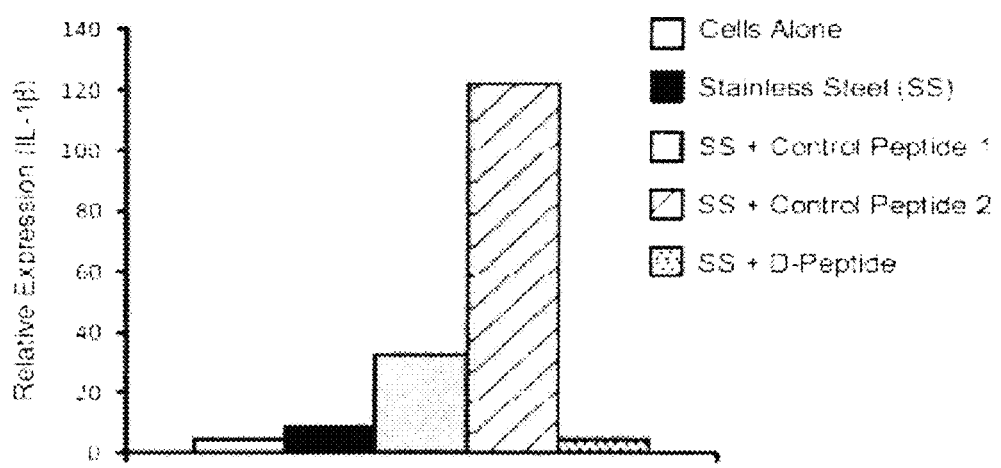

A similar study was conducted to test the inflammatory response of human THP-1 macrophage cells against the same samples, but including additional samples formed of stainless steel or titanium coated with control peptides 1 or 2 that represent non-binding pilin peptide sequences. The coated and uncoated samples were then incubated with THP-1 macrophages in RPMI medium at 37° C. for 72 hours. The culture media and cellular lysates were then assayed for the cytokine IL-1β and the housekeeping protein tubulin. The results are given in the two Western blots in FIG. 26A. As seen, titanium alone provoked a strong inflammatory response that was substantially diminished by the D-form pilin coating. The more quantitative picture for the stainless steel sample given in FIG. 26B shows that, although the inflammatory response to uncoated stainless steel was rather small, the effect was nonetheless inhibited by the D-peptide coating. It is apparent from the two control-peptide samples, which show a moderate and strong response, that the effect of D-form pilin coating is quite specific.

In one aspect, the invention includes a medical device having surfaces that are exposed to inflammatory-response cells when implanted in a body, in which these surfaces are coated with a synthetic pilin peptide containing (i) a disulfide loop derived from the C-terminal receptor binding protein of Type IV P. aeruginosa (T4P) pilin, (ii) 0-10, preferably 0-5, additional residues on either the N- or C-terminal side of the loop, and (iii) composed of D-amino acids, mixture of D- and L-amino acids, or D-amino acids in a retro-inverso (RI) form.

Figure 24A:
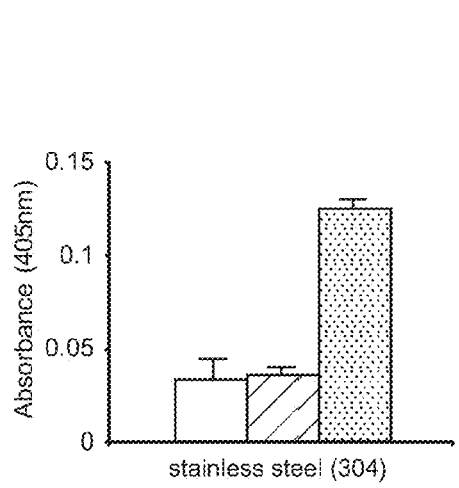
FIGS. 24A-24D are bar graphs showing binding of T4P17 pilin peptide to stainless steel (24A), a coronary stent (24B), a Foley (latex) catheter (24C), and a central venous (silicone) (24D) catheter.
Figure 24B:
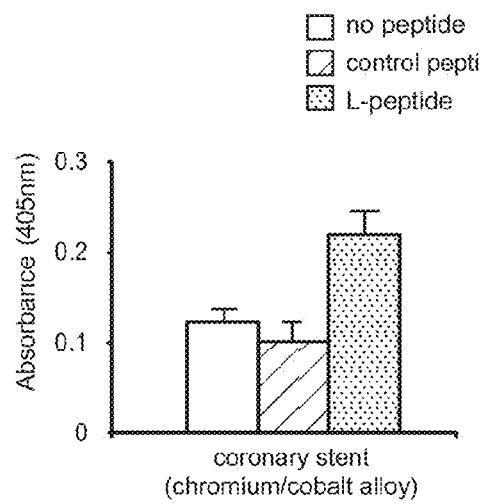
Figure 24C:
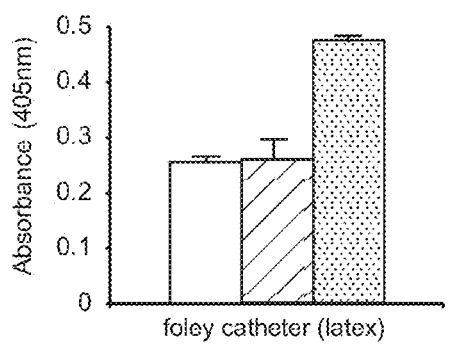
Figure 24D:
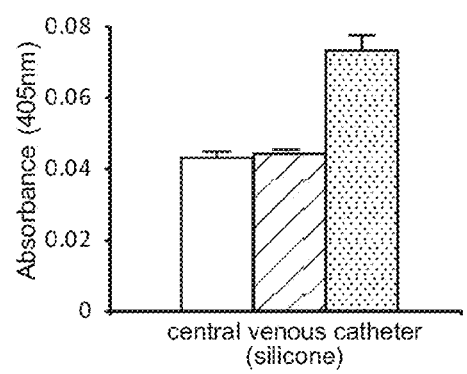

The binding studies in FIGS. 24A-24D demonstrate a strong bonding of a D-form pilin peptide to a variety of medical devices and device surfaces, including stainless steel (FIG. 24A), a chromium cobalt stent (FIG. 24B), a latex catheter (FIG. 24C), and a silicone venous catheter (FIG. 24D). In each case, a sample was either uncoated (open bars in FIG. 24), coated with a control scrambled pilin sequence (shaded bars), or a D-form pilin peptide. The samples were then washed and assayed for bound protein by the HRT assay described above. For all samples, the levels of bound pilin peptide were substantially above control levels, with stainless steel appearing to form the most highly bonded coating. The invention includes other medical devices that are implanted or temporarily implanted in a subject body, including both metal and non-metal stents, catheters formed of a variety of flexible and materials, appliances supported at the end of catheters, and heart and other vascular valves, where the device includes surfaces exposed an inflammatory response in the body and is coated with a D-form or RI form pilin peptide.

In a related aspect, the invention also includes a method of inhibiting an inflammatory response against a medical device implanted in a subject by, prior to implanting the device, coating exposed surfaces of the device with a synthetic pilin peptide containing (i) a disulfide loop derived from the C-terminal receptor binding protein of Type IV P. aeruginosa (T4P) pilin, (ii) 0-10, preferably 0-5 additional residues on either or both the N- or C-terminal side of the loop, and (iii) composed of D-amino acids, mixture of D- and L-amino acids, or D-amino acids in a retro-inverso (RI) form.

Although the invention has been described with respect to specific embodiments and applications, it will be appreciated with various modifications can be made without departing from the invention.

FIG. 1A

```
                                              SEQ ID NO: 1
G7-G9  SIDWGCASDSNAVSSGTDRNMPALTAGTLPARFAPSECR
                                              SEQ ID NO: 2
PA110594  TIDWACTSASNAT--ATAQGFTGMAAGSVPQEFAPAQCR
                                              SEQ ID NO: 3
PAO  DGVWACKSTQDPMFTPKGCDN
                                              SEQ ID NO: 4
PAK  DGLWKCTSDQDEQFIPKGCSR
                                              SEQ ID NO: 5
PA1244  DGVWNCKITKTPTAWKPNYAPANCPKS
                                              SEQ ID NO: 6
PA5658  EGVWTCATSGSPANWKANYAPANCPKS
                                              SEQ ID NO: 7
PA82935  NGGWSCATTVDAKFRPNGCTD
                                              SEQ ID NO: 8
PA5196  GSSWACGNASIDGFAGTGTTIDAKYLPNACKP
                                              SEQ ID NO: 9
K122-4  SYTWACTSNADNKYLPKTCQTATTTTP
                                              SEQ ID NO: 10
Composite:  K/A/S/T-C-T/K/A-S/T-D/T/N-Q/V/A-D/E-E/
P/A/N-Q/M/K-F/Y-I/T/R/L-P-K/N-G/T-C-S/D/T/Q/N-K/
N/D/T
                                              SEQ ID NO: 11
Composite:  S/T-I-D-W-G/A-C-A/T-S-D/A-S-N-A-V/T-S/
--S--G/A-T-D/A-R/Q-N/G-M/F-P/T-A/G-L/M-T/A-A-G-T/
S-L/V-P-A/Q-R/E-F-A-P-S/A-E/Q-C-R
```

FIG. 1B

```
                                              SEQ ID NO: 11
K122-4      SYTWACT  S----NADNKYLPKTCQTA-----TTTTP
                                              SEQ ID NO: 12
Rmet2278954 SVTWQCE  S----SADKRYVPQACAKASESGKTTTTT
                                              SEQ ID NO: 13
Ncin7259486 SFSWVCK  KGTSDSVDDKFLPSSCRTA-----ATTTAG
                                              SEQ ID NO: 14
Ecor729393  SFSWECS  S----NADAKYLPSSCRNA-----ATPTPT
```

FIG. 1C

```
                                                    SEQ ID NO: 15
PA5196       GSSWACGNASIDG--------FAGTGTTIDAKYLPNACKP----
----

SEQ ID NO: 16
Ecor729393   SFSWECSS------------------NADAKYLPSSCRN
AATPTPTP
                                                    SEQ ID NO: 17
Ngon95402    SVKWFCGQPVTRTGDNDDTVADAKDGKEIDTKHLPSTCRDT
SSAGK-
                                                    SEQ ID NO: 18
Xcam21232529 SISWGCTN-----------------GTTIDQKYLPTSC
RTAAAP----
```

FIG. 1D

```
                                                    SEQ ID NO: 19
PA82935      NGGWSCATTVDAKFRPNGCTD----

SEQ ID NO: 20
Dnod120452   SGSWYCHSNAAEKFLPSGCKYDASL

SEQ ID NO: 19
PA82935      NGGWSCATTVDAKFRPNGCTD----

SEQ ID NO: 20
Dnod120452   SGSWYCHSNAAEKFLPSGCKYDASL
```

Rmet = Ralsonia metallidurans GI 2278954
Ncin = Neisseria cinera GI 7259486
Ecor = Eikenella corrodens GI 729393
Ngon = Neisseria gonorrhoeae GI 95402
Xcam = Xanthomonas cmpestris GI 21232529
Dnod = Dichelobacter nodosus GI 120452

---

It is claimed:

1. A method of covalently attaching a compound to one or more exposed surfaces of a substrate formed of stainless steel, tin, iron, or titanium, comprising
contacting exposed surface(s) of the substrate with a synthetic pilin peptide containing a disulfide loop having the sequence identified as SEQ ID NO:10 and containing 0-10 additional residues on either or both the N- or C-terminal side of the loop, thereby to bind the pilin peptide covalently to the exposed surface(s), and
before or after said contacting and binding, covalently attaching the compound to the pilin peptide.

2. The method of claim 1, wherein the substrate surfaces have exposed grain boundary regions, and said contacting is effective to preferentially localize said compound at exposed grain boundary regions.

3. The method of claim 1, wherein the pilin peptide is formed with L-amino acids.

4. The method of claim 1, wherein the pilin peptide is formed with D-amino acids, a mixture of L- and D-amino acids, or with D-amino acids in a retro-inverso (RI) form.

5. The method of claim 1, wherein the pilin peptide contains the sequence identified as SEQ ID NOS:3, 4, or 9.

6. The method of claim 1, wherein the compound is selected from the group consisting of peptides, oligosaccharides, lipids, nucleic acids, and small organic molecules.

7. The method of claim 1, wherein said material is porous or reticulated, and said contacting is effective to bind the pilin peptide to internal surfaces defined by pores or reticulations in the material.

8. A stainless steel, tin, iron, or titanium substrate with a covalently attached compound formed by the method of claim 1, wherein the substrate has an altered electron work function by virtue of the binding of the pilin peptide to the substrate surface and the compound is covalently attached to the pilin peptide.

9. The substrate of claim 8, which is part of an implantable medical device.

10. In a method of treating stainless steel, tin, iron, or titanium metal material having surfaces with exposed grain boundary regions, to reduce the rate of corrosion or the material, an improvement comprising
contacting exposed surfaces boundary regions in the material with a synthetic pilin peptide containing a disulfide loop having the sequence identified as SEQ ID NO:10 and containing 0-10 additional residues on either or both the N- or C-terminal side of the loop, under conditions effective to change the electron work function of exposed grain-boundary regions by at least 0.2 EFW units and to increase the hardness of exposed grain-boundary regions, as measured by nano-indentation produced by striking the metal surface with the tip of an atomic force microscope with a given force, by at least 20%.

11. The improvement of claim 10, wherein the metal material is stainless steel, and the contacting step is effective to reduce the rate of corrosion of the coated surface, as measured by the corrosion current across the surface by at least 30%.

12. The improvement of claim 10, wherein the metal material is porous or reticulated, and the contacting step is be carried out to bind the pilin peptide to internal surfaces defined by pores or reticulations in the material.

13. The improvement of claim 10, wherein the metal material has exposed grain-boundary regions, and the contacting step is effective to bind the pilin peptide selectively to said grain boundary regions, thus enhancing the hardness and corrosion resistance of the metal surface by preferentially protecting the surface at its grain boundary regions.

14. The improvement of claim 10, wherein the pilin peptide is formed with L-amino acids.

15. The improvement of claim 10, wherein the pilin peptide is formed of D-amino acids, a mixture of L- and D-amino acids, or D-amino acids in a retro-inverso (RI) form.

16. The improvement of claim 10, wherein the pilin peptide contains the sequence identified as SEQ ID NOS:3, 4, or 9.

17. A method of inhibiting an inflammatory response against a medical device that is designed to be implanted in a subject, comprising,
prior to implanting the device, coating exposed surfaces of the device with a synthetic pilin peptide containing (i) a disulfide having the sequence identified as SEQ ID NO:10 (ii) 0-10 additional residues on either or both the N- or C-terminal side of the loop, and (iii) composed of D-amino acids, mixture of D- and L-amino acids, or D-amino acids in a retro-inverso (RI) form.

18. The method of claim 17, wherein the pilin peptide contains the sequence identified as SEQ ID NOS:3, 4, or 9.

19. The method of claim 17, wherein the medical device is one of (i) an in-dwelling catheter having a tube whose outer surface is coated with the pilin peptide, (ii) a prosthetic device having an external stainless steel, tin, iron, or titanium surface that is coated with the pilin peptide, and (iii) an intravascular stent having an external stainless steel, titanium, or polymer surface that is coated with the pilin peptide.

20. A medical device having surfaces that are exposed to inflammatory-response cells when implanted in a body, in which such surfaces are coated with a synthetic pilin peptide containing (i) a disulfide loop having the sequence identified as SEQ ID NO:10, (ii) 0-10 additional residues on either or both the N- or C-terminal side of the loop, and (iii) composed of D-amino acids, mixture of D- and L-amino acids, or D-amino acids in a retro-inverso (RI) form.

21. The device of claim 20, wherein the surfaces exposed to inflammatory response cells, after implantation, are stainless steel, tin, iron, or titanium surfaces.

* * * * *

SEQUENCE LISTING

```
<160> NUMBER OF SEQ ID NOS: 21

<210> SEQ ID NO 1
<211> LENGTH: 39
<212> TYPE: PRT
<213> ORGANISM: Pseudomonas aeroginosa

<400> SEQUENCE: 1

Ser Ile Asp Trp Gly Cys Ala Ser Asp Ser Asn Ala Val Ser Ser Gly
1               5                   10                  15

Thr Asp Arg Asn Met Pro Ala Leu Thr Ala Gly Thr Leu Pro Ala Arg
            20                  25                  30

Phe Ala Pro Ser Glu Cys Arg
        35

<210> SEQ ID NO 2
<211> LENGTH: 37
<212> TYPE: PRT
<213> ORGANISM: Pseudomonas aeroginosa

<400> SEQUENCE: 2

Thr Ile Asp Trp Ala Cys Thr Ser Ala Ser Asn Ala Thr Ala Thr Ala
1               5                   10                  15

Gln Gly Phe Thr Gly Met Ala Ala Gly Ser Val Pro Gln Glu Phe Ala
            20                  25                  30

Pro Ala Gln Cys Arg
        35

<210> SEQ ID NO 3
<211> LENGTH: 21
<212> TYPE: PRT
<213> ORGANISM: Pseudomonas aeroginosa

<400> SEQUENCE: 3

Asp Gly Val Trp Ala Cys Lys Ser Thr Gln Asp Pro Met Phe Thr Pro
1               5                   10                  15

Lys Gly Cys Asp Asn
            20

<210> SEQ ID NO 4
<211> LENGTH: 21
<212> TYPE: PRT
<213> ORGANISM: Pseudomonas aeroginosa
```

```
<400> SEQUENCE: 4

Asp Gly Leu Trp Lys Cys Thr Ser Asp Gln Asp Glu Gln Phe Ile Pro
1               5                   10                  15

Lys Gly Cys Ser Arg
            20

<210> SEQ ID NO 5
<211> LENGTH: 27
<212> TYPE: PRT
<213> ORGANISM: Pseudomonas aeroginosa

<400> SEQUENCE: 5

Asp Gly Val Trp Asn Cys Lys Ile Thr Lys Thr Pro Thr Ala Trp Lys
1               5                   10                  15

Pro Asn Tyr Ala Pro Ala Asn Cys Pro Lys Ser
            20                  25

<210> SEQ ID NO 6
<211> LENGTH: 27
<212> TYPE: PRT
<213> ORGANISM: Pseudomonas aeroginosa

<400> SEQUENCE: 6

Glu Gly Val Trp Thr Cys Ala Thr Ser Gly Pro Ala Asn Trp Lys
1               5                   10                  15

Ala Asn Tyr Ala Pro Ala Asn Cys Pro Lys Ser
            20                  25

<210> SEQ ID NO 7
<211> LENGTH: 21
<212> TYPE: PRT
<213> ORGANISM: Pseudomonas aeroginosa

<400> SEQUENCE: 7

Asn Gly Gly Trp Ser Cys Ala Thr Thr Val Asp Ala Lys Phe Arg Pro
1               5                   10                  15

Asn Gly Cys Thr Asp
            20

<210> SEQ ID NO 8
<211> LENGTH: 32
<212> TYPE: PRT
<213> ORGANISM: Pseudomonas aeroginosa

<400> SEQUENCE: 8

Gly Ser Ser Trp Ala Cys Gly Asn Ala Ser Ile Asp Gly Phe Ala Gly
1               5                   10                  15

Thr Gly Thr Thr Ile Asp Ala Lys Tyr Leu Pro Asn Ala Cys Lys Pro
            20                  25                  30

<210> SEQ ID NO 9
<211> LENGTH: 27
<212> TYPE: PRT
<213> ORGANISM: Pseudomonas aeroginosa

<400> SEQUENCE: 9

Ser Tyr Thr Trp Ala Cys Thr Ser Asn Ala Asp Asn Lys Tyr Leu Pro
1               5                   10                  15

Lys Thr Cys Gln Thr Ala Thr Thr Thr Pro
            20                  25
```

-continued

```
<210> SEQ ID NO 10
<211> LENGTH: 17
<212> TYPE: PRT
<213> ORGANISM: Artificial
<220> FEATURE:
<223> OTHER INFORMATION: synthetic consensus sequence
<220> FEATURE:
<221> NAME/KEY: misc_feature
<222> LOCATION: (1)..(1)
<223> OTHER INFORMATION: Xaa is Lys, Ala, Ser or Thr
<220> FEATURE:
<221> NAME/KEY: misc_feature
<222> LOCATION: (3)..(3)
<223> OTHER INFORMATION: Xaa is Thr, Lys or Ala
<220> FEATURE:
<221> NAME/KEY: misc_feature
<222> LOCATION: (4)..(4)
<223> OTHER INFORMATION: Xaa is Ser or Thr
<220> FEATURE:
<221> NAME/KEY: misc_feature
<222> LOCATION: (5)..(5)
<223> OTHER INFORMATION: Xaa is Asp, Thr or Asn
<220> FEATURE:
<221> NAME/KEY: misc_feature
<222> LOCATION: (6)..(6)
<223> OTHER INFORMATION: Xaa is Gln, Val or Ala
<220> FEATURE:
<221> NAME/KEY: misc_feature
<222> LOCATION: (7)..(7)
<223> OTHER INFORMATION: Xaa is Asp or Glu
<220> FEATURE:
<221> NAME/KEY: misc_feature
<222> LOCATION: (8)..(8)
<223> OTHER INFORMATION: Xaa is Glu, Pro, Ala or Asn
<220> FEATURE:
<221> NAME/KEY: misc_feature
<222> LOCATION: (9)..(9)
<223> OTHER INFORMATION: Xaa is Gln, Met or Lys
<220> FEATURE:
<221> NAME/KEY: misc_feature
<222> LOCATION: (10)..(10)
<223> OTHER INFORMATION: Xaa is Phe or Tyr
<220> FEATURE:
<221> NAME/KEY: misc_feature
<222> LOCATION: (11)..(11)
<223> OTHER INFORMATION: Xaa is Ile, Thr, Arg or Leu
<220> FEATURE:
<221> NAME/KEY: misc_feature
<222> LOCATION: (13)..(13)
<223> OTHER INFORMATION: Xaa is Lys or Asn
<220> FEATURE:
<221> NAME/KEY: misc_feature
<222> LOCATION: (14)..(14)
<223> OTHER INFORMATION: Xaa is Gly or Thr
<220> FEATURE:
<221> NAME/KEY: misc_feature
<222> LOCATION: (16)..(16)
<223> OTHER INFORMATION: Xaa is Ser, Asp, Thr, Gln or Asn
<220> FEATURE:
<221> NAME/KEY: misc_feature
<222> LOCATION: (17)..(17)
<223> OTHER INFORMATION: Xaa is Lys, Asn, Asp or Thr

<400> SEQUENCE: 10

Xaa Cys Xaa Xaa Xaa Xaa Xaa Xaa Xaa Xaa Pro Xaa Xaa Cys Xaa
1               5                   10                  15

Xaa

<210> SEQ ID NO 11
<211> LENGTH: 27
<212> TYPE: PRT
<213> ORGANISM: Pseudomonas aeroginosa

<400> SEQUENCE: 11
```

-continued

Ser Tyr Thr Trp Ala Cys Thr Ser Asn Ala Asp Asn Lys Tyr Leu Pro
1               5                   10                  15

Lys Thr Cys Gln Thr Ala Thr Thr Thr Pro
            20                  25

<210> SEQ ID NO 12
<211> LENGTH: 33
<212> TYPE: PRT
<213> ORGANISM: Ralsonia metallidurans

<400> SEQUENCE: 12

Ser Val Thr Trp Gln Cys Glu Ser Ser Ala Asp Lys Arg Tyr Val Pro
1               5                   10                  15

Gln Ala Cys Ala Lys Ala Ser Glu Ser Gly Lys Thr Thr Thr Thr Thr
            20                  25                  30

Thr

<210> SEQ ID NO 13
<211> LENGTH: 32
<212> TYPE: PRT
<213> ORGANISM: Neisseria cinera

<400> SEQUENCE: 13

Ser Phe Ser Trp Val Cys Lys Lys Gly Thr Ser Asp Ser Val Asp Asp
1               5                   10                  15

Lys Phe Leu Pro Ser Ser Cys Arg Thr Ala Ala Thr Thr Thr Ala Gly
            20                  25                  30

<210> SEQ ID NO 14
<211> LENGTH: 28
<212> TYPE: PRT
<213> ORGANISM: Eikenella corrodens

<400> SEQUENCE: 14

Ser Phe Ser Trp Glu Cys Ser Ser Asn Ala Asp Ala Lys Tyr Leu Pro
1               5                   10                  15

Ser Ser Cys Arg Asn Ala Ala Thr Pro Thr Pro Thr
            20                  25

<210> SEQ ID NO 15
<211> LENGTH: 32
<212> TYPE: PRT
<213> ORGANISM: Pseudomonas aeroginosa

<400> SEQUENCE: 15

Gly Ser Ser Trp Ala Cys Gly Asn Ala Ser Ile Asp Gly Phe Ala Gly
1               5                   10                  15

Thr Gly Thr Thr Ile Asp Ala Lys Tyr Leu Pro Asn Ala Cys Lys Pro
            20                  25                  30

<210> SEQ ID NO 16
<211> LENGTH: 29
<212> TYPE: PRT
<213> ORGANISM: Eikenella corrodens

<400> SEQUENCE: 16

Ser Phe Ser Trp Glu Cys Ser Ser Asn Ala Asp Ala Lys Tyr Leu Pro
1               5                   10                  15

Ser Ser Cys Arg Asn Ala Ala Thr Pro Thr Pro Thr Pro
            20                  25

```
<210> SEQ ID NO 17
<211> LENGTH: 46
<212> TYPE: PRT
<213> ORGANISM: Neisseria gonorrhoeae

<400> SEQUENCE: 17

Ser Val Lys Trp Phe Cys Gly Gln Pro Val Thr Arg Thr Gly Asp Asn
1               5                   10                  15

Asp Asp Thr Val Ala Asp Ala Lys Gly Lys Glu Ile Asp Thr Lys
            20                  25                  30

His Leu Pro Ser Thr Cys Arg Asp Thr Ser Ser Ala Gly Lys
        35                  40                  45

<210> SEQ ID NO 18
<211> LENGTH: 27
<212> TYPE: PRT
<213> ORGANISM: Xanthomonas cmpestris

<400> SEQUENCE: 18

Ser Ile Ser Trp Gly Cys Thr Asn Gly Thr Thr Ile Asp Gln Lys Tyr
1               5                   10                  15

Leu Pro Thr Ser Cys Arg Thr Ala Ala Ala Pro
            20                  25

<210> SEQ ID NO 19
<211> LENGTH: 21
<212> TYPE: PRT
<213> ORGANISM: Pseudomonas aeroginosa

<400> SEQUENCE: 19

Asn Gly Gly Trp Ser Cys Ala Thr Thr Val Asp Ala Lys Phe Arg Pro
1               5                   10                  15

Asn Gly Cys Thr Asp
            20

<210> SEQ ID NO 20
<211> LENGTH: 25
<212> TYPE: PRT
<213> ORGANISM: Dichelobacter nodosus

<400> SEQUENCE: 20

Ser Gly Ser Trp Tyr Cys His Ser Asn Ala Ala Glu Lys Phe Leu Pro
1               5                   10                  15

Ser Gly Cys Lys Tyr Asp Ala Ser Leu
            20                  25

<210> SEQ ID NO 21
<211> LENGTH: 39
<212> TYPE: PRT
<213> ORGANISM: Artificial
<220> FEATURE:
<223> OTHER INFORMATION: synthetic consensus sequence
<220> FEATURE:
<221> NAME/KEY: misc_feature
<222> LOCATION: (1)..(1)
<223> OTHER INFORMATION: Xaa is Ser or Thr
<220> FEATURE:
<221> NAME/KEY: misc_feature
<222> LOCATION: (5)..(5)
<223> OTHER INFORMATION: Xaa is Gly or Ala
<220> FEATURE:
<221> NAME/KEY: misc_feature
<222> LOCATION: (7)..(7)
<223> OTHER INFORMATION: Xaa is Ala or Thr
<220> FEATURE:
<221> NAME/KEY: misc_feature
```

```
<222> LOCATION: (9)..(9)
<223> OTHER INFORMATION: Xaa is Asp or Ala
<220> FEATURE:
<221> NAME/KEY: misc_feature
<222> LOCATION: (13)..(13)
<223> OTHER INFORMATION: Xaa is Val or Thr
<220> FEATURE:
<221> NAME/KEY: misc_feature
<222> LOCATION: (14)..(14)
<223> OTHER INFORMATION: Xaa is Ser or may be absent
<220> FEATURE:
<221> NAME/KEY: misc_feature
<222> LOCATION: (15)..(15)
<223> OTHER INFORMATION: Xaa is Ser or may be absent
<220> FEATURE:
<221> NAME/KEY: misc_feature
<222> LOCATION: (16)..(16)
<223> OTHER INFORMATION: Xaa is Gly or Ala
<220> FEATURE:
<221> NAME/KEY: misc_feature
<222> LOCATION: (18)..(18)
<223> OTHER INFORMATION: Xaa is Asp or Ala
<220> FEATURE:
<221> NAME/KEY: misc_feature
<222> LOCATION: (19)..(19)
<223> OTHER INFORMATION: Xaa is Arg or Gln
<220> FEATURE:
<221> NAME/KEY: misc_feature
<222> LOCATION: (20)..(20)
<223> OTHER INFORMATION: Xaa is Asn or Gly
<220> FEATURE:
<221> NAME/KEY: misc_feature
<222> LOCATION: (21)..(21)
<223> OTHER INFORMATION: Xaa is Met or Phe
<220> FEATURE:
<221> NAME/KEY: misc_feature
<222> LOCATION: (22)..(22)
<223> OTHER INFORMATION: Xaa is Pro or Thr
<220> FEATURE:
<221> NAME/KEY: misc_feature
<222> LOCATION: (23)..(23)
<223> OTHER INFORMATION: Xaa is Ala or Gly
<220> FEATURE:
<221> NAME/KEY: misc_feature
<222> LOCATION: (24)..(24)
<223> OTHER INFORMATION: Xaa is Leu or Met
<220> FEATURE:
<221> NAME/KEY: misc_feature
<222> LOCATION: (25)..(25)
<223> OTHER INFORMATION: Xaa is Thr or Ala
<220> FEATURE:
<221> NAME/KEY: misc_feature
<222> LOCATION: (28)..(28)
<223> OTHER INFORMATION: Xaa is Thr or Ser
<220> FEATURE:
<221> NAME/KEY: misc_feature
<222> LOCATION: (29)..(29)
<223> OTHER INFORMATION: Xaa is Leu or Val
<220> FEATURE:
<221> NAME/KEY: misc_feature
<222> LOCATION: (31)..(31)
<223> OTHER INFORMATION: Xaa is Ala or Gln
<220> FEATURE:
<221> NAME/KEY: misc_feature
<222> LOCATION: (32)..(32)
<223> OTHER INFORMATION: Xaa is Arg or Glu
<220> FEATURE:
<221> NAME/KEY: misc_feature
<222> LOCATION: (36)..(36)
<223> OTHER INFORMATION: Xaa is Ser or Ala
<220> FEATURE:
<221> NAME/KEY: misc_feature
<222> LOCATION: (37)..(37)
<223> OTHER INFORMATION: Xaa is Glu or Gln

<400> SEQUENCE: 21

Xaa Ile Asp Trp Xaa Cys Xaa Ser Xaa Ser Asn Ala Xaa Xaa Xaa Xaa
1               5                   10                  15
```

-continued

```
Thr Xaa Xaa Xaa Xaa Xaa Xaa Xaa Xaa Ala Gly Xaa Xaa Pro Xaa Xaa
        20                  25                  30
Phe Ala Pro Xaa Xaa Cys Arg
        35
```